(12) United States Patent
Bernard et al.

(10) Patent No.: US 11,954,853 B2
(45) Date of Patent: Apr. 9, 2024

(54) SYSTEMS AND METHODS FOR FAST MAMMOGRAPHY DATA HANDLING

(71) Applicant: GE Precision Healthcare LLC, Milwaukee, WI (US)

(72) Inventors: Sylvain Bernard, Montigny le Bretonneux (FR); Vincent Bismuth, Yvelines (FR)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 365 days.

(21) Appl. No.: 17/382,159

(22) Filed: Jul. 21, 2021

(65) Prior Publication Data
US 2023/0023042 A1 Jan. 26, 2023

(51) Int. Cl.
*G06T 7/00* (2017.01)
*G06N 3/08* (2023.01)
*G06N 3/084* (2023.01)
*G16H 30/40* (2018.01)

(52) U.S. Cl.
CPC ........... *G06T 7/0012* (2013.01); *G06N 3/084* (2013.01); *G16H 30/40* (2018.01); *G06T 2207/20081* (2013.01); *G06T 2207/20084* (2013.01); *G06T 2207/30068* (2013.01)

(58) Field of Classification Search
CPC ......... G06T 7/0012; G06T 2207/20081; G06T 2207/20084; G06T 2207/30068; G16H 30/40; G06N 3/084
See application file for complete search history.

(56) References Cited

U.S. PATENT DOCUMENTS

| 6,091,841 A | 7/2000 | Rogers et al. |
| 10,885,400 B2 | 1/2021 | Zhao et al. |
| 2020/0058126 A1 | 2/2020 | Wang |

OTHER PUBLICATIONS

Bhatti et al, "Multi-detection and Segmentation of Breast Lesions Based on Mask RCNN-FPN", 2020, IEEE International Conference on Bioinformatics and Biomedicine (BIBM), pp. 2698-2704 (7 pages) (Year: 2020).*

Ertas et al, "Breast MR segmentation and lesion detection with cellular neural networks and 3D template matching", 2008, Computers in Biology and Medicine 38, pp. 116-126 (11 pages) (Year: 2008).*

(Continued)

*Primary Examiner* — David F Dunphy
(74) *Attorney, Agent, or Firm* — McCoy Russell LLP

(57) ABSTRACT

This disclosure proposes to speed up computation time of a convolutional neural network (CNN) by leveraging information specific to a pre-defined region, such as a breast in mammography and tomosynthesis data. In an exemplary embodiment, a method for an image processing system is provided, comprising, generating an output of a trained convolutional neural network (CNN) of the image processing system based on an input image, including a pre-defined region of the input image as an additional input into at least one of a convolutional layer and a fully connected layer of the CNN to limit computations to input image data inside the pre-defined region; and storing the output and/or displaying the output on a display device.

17 Claims, 8 Drawing Sheets

(56) References Cited

OTHER PUBLICATIONS

Zhu, W. et al., "Deep Multi-instance Networks with Sparse Label Assignment for Whole Mammogram Classification," Cornell University arXiv Website, Available Online at https://arxiv.org/abs/1612.05968, Available as Early as Dec. 18, 2016, 8 pages.
Harley, A. et al., "Segmentation-Aware Convolutional Networks Using Local Attention Masks," Cornell University arXiv Website, Available Online at https://arxiv.org/abs/1708.04607, Available as Early as Aug. 15, 2017, 11 pages.
Eppel, S., "Setting an attention region for convolutional neural networks using region selective features, for recognition of materials within glass vessels," Cornell University arXiv Website, Available Online at https://arxiv.org/abs/1708.08711, Available as Early as Aug. 29, 2017, 20 pages.
Shen, L. et al., "Deep Learning to Improve Breast Cancer Detection on Screening Mammography," Scientific Reports, vol. 9, No. 12495, Aug. 29, 2019, 12 pages.
JP patent application 2022-110877 filed Jul. 11, 2022—Office Action dated Jun. 7, 2023; Machine Translation; 6 pages.
EP application 22182923.7 filed Jul. 4, 2022—extended Search Report dated Dec. 16, 2022, 11 pages.
Fan Ming et al: "Computer-aided detection of mass in digital breast tomosynthesis using a faster region-based convolutional neural network", Methods, Academic Press, NL, vol. 166, Feb. 13, 2019 (Feb. 13, 2019), pp. 103-111, XP085782110, ISSN: 1046-2023, DOI: 10.1016/J.YMETH.2019.02.010 [retrieved on Feb. 13, 2019].
Min Hang et al: "Fully Automatic Computer-aided Mass Detection and Segmentation via Pseudo-color Mammograms and Mask R-CNN", 2020 IEEE 17th International Symposium on Biomedical Imaging (ISBI), IEEE, Apr. 3, 2020 (Apr. 3, 2020), pp. 1111-1115, XP033773842, DOI: 10.1109/ISBI45749.2020.9098732 [retrieved on May 21, 2020].

\* cited by examiner

SYSTEMS AND METHODS FOR FAST MAMMOGRAPHY DATA HANDLING

TECHNICAL FIELD

Embodiments of the subject matter disclosed herein relate to medical imaging, and more particularly, to systems and methods for classifying medical images using deep learning neural networks.

BACKGROUND

Deep learning techniques have shown outstanding performances for visual recognition in many vision tasks. Neural networks may be pre-trained on large-scale datasets, such as ImageNet databases, to develop powerful visual descriptors referred to as Deep Features (DFs). DFs may constitute core building blocks that may be used in subsequent training to achieve improved performance on vision tasks. However, while ImageNet images are typically lower resolution (e.g., 224*224 pixel) images, Full Field Digital Mammography (FFDM) images may have significantly higher resolution (e.g., 2394*2850 pixels), and Digital Breast Tomosynthesis (DBT) image volumes may include up to 50 times more data. As a result of the much larger amount of data in FFDM and DBT images, a computation time during training and inference times may be impractically long for high resolution images.

SUMMARY

The current disclosure at least partially addresses one or more of the above identified issues by a method for an image processing system, comprising, generating an output of a trained convolutional neural network (CNN) of the image processing system based on an input image, including a pre-defined region of the input image as an additional input into at least one of a convolutional layer and a fully connected layer of the CNN to limit computations to input image data inside the pre-defined region; and storing the output and/or displaying the output on a display device. The pre-defined region may be defined using one or more masks, which may also be used during training of the CNN, in a first, forward pass of a training cycle, to activate neurons at each layer of the CNN based on image data within the pre-defined region and not by image data outside the pre-defined region. Further, the one or more masks may be used during backpropagation, where a difference between an output and a target may be backpropagated through each layer of the CNN, and weights associated with each neuron of each layer of the CNN may be adjusted based on data of pre-defined region and not based on background data. By constraining error backpropagation and weight adjustments to data from the pre-defined region, and not from an area outside the pre-defined region, a performance of the CNN may be improved and a computation time of training may be reduced, as compared with inputting a full size image into the CNN. By using the one or more masks during a subsequent inference stage, a running time of the CNN may be reduced without a performance tradeoff, leading to faster diagnoses and improved patient outcomes. The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

Figure 1:
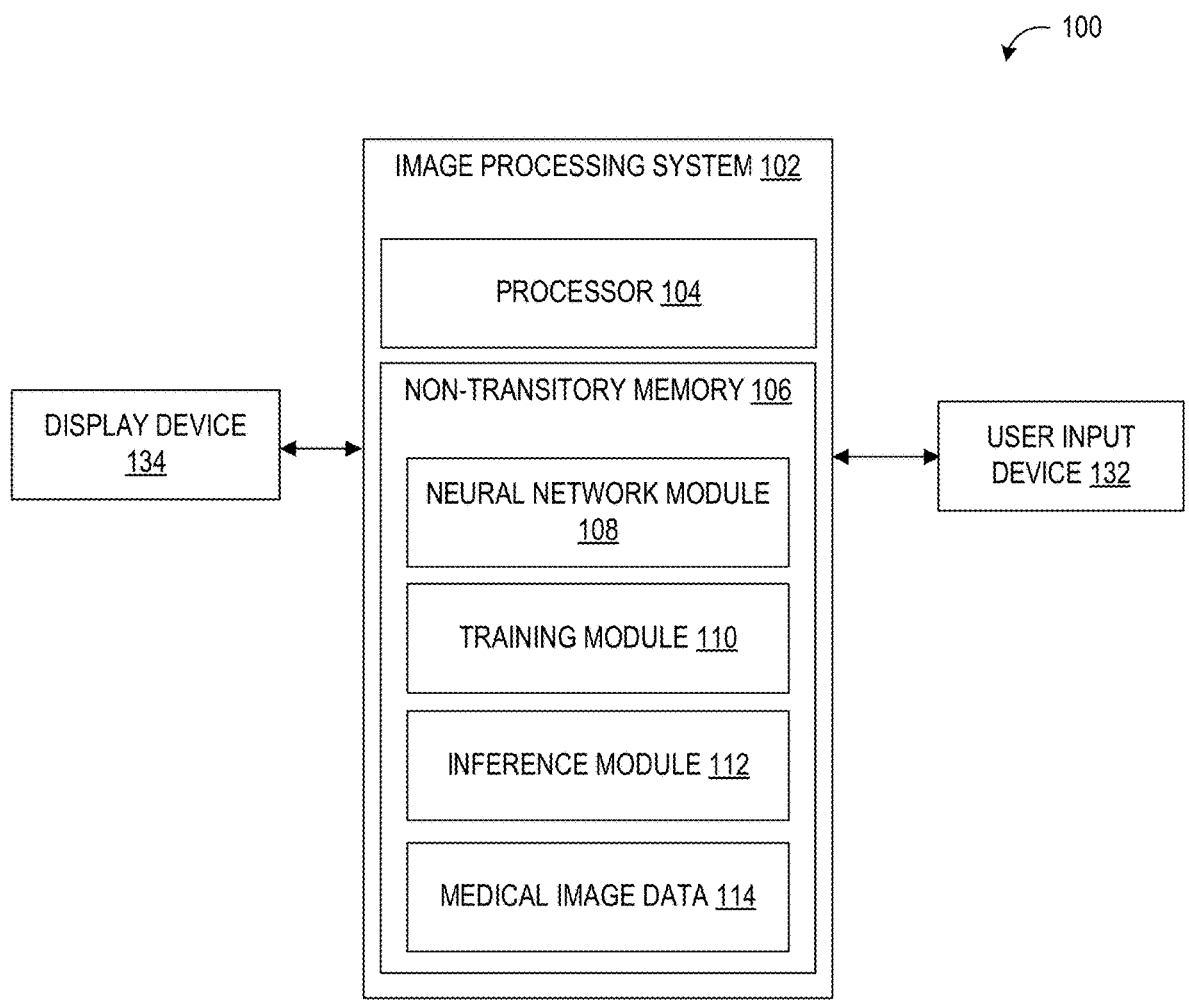
FIG. 1 shows a block diagram of an exemplary embodiment of an image processing system.

The drawings illustrate specific aspects of the described systems and methods for mapping one or more medical images in a first resolution to one or more corresponding medical images in a target resolution using generative neural networks. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

Methods and systems are provided herein for reducing convolutional neural network (CNN) computation time when processing mammography and tomosynthesis data, without a tradeoff between speed and performance. Typical applications include cancer/non-cancer breast classification (negative triage), automatic lesion detection (CAD), and AI based image processing where a high-resolution mammogram image is provided as an input to the CNN.

One way to reduce computation time is to eliminate non-relevant pixel data. Breast pixels typically occupy one third of a detector surface, and computation time may be reduced by not processing background pixels of an image. One approach includes feeding a convolutional neural network (CNN) images cropped to a breast bounding box.

However, while a size of an input layer of the CNN is typically fixed, bounding box sizes may vary, as a footprint of a breast on the detector may vary from one patient to another and from one acquisition to another. As a consequence, cropped input images may have to be resized in order to fit the network input size, for example, by zooming in or out on the input image. Moreover, since the bounding box is not square, a non-isotropic zoom factor may be applied for a majority of the breasts. A resulting change in image resolution and distortion due to non-isotropic zoom may impact a performance of the CNN, especially when dealing with tiny objects, such as micro-calcifications, with a resolution close to a detector resolution.

Another approach is to use a mask to eliminate pixel data outside a boundary of the mask. For example, an array of 1s and 0s corresponding to pixels of an image may be included as an additional input of the CNN along with the image, where pixels including a breast are assigned 1s and pixels not including the breast (e.g., a background) are assigned 0s. During convolution operations of the input layer, neurons of the input layer may only be activated for the pixels including the breast, and not for the pixels not including the breast. However, including a mask at the input layer of the CNN may not sufficiently reduce computation time during training and/or deployment of the CNN to facilitate widespread adoption of AI models for FFDM and DBT data.

As described herein, computation time may be further reduced in both training and inference stages by leveraging prior knowledge of the breast area at each layer of the CNN. In other words, in addition to applying a mask at an input layer of the CNN, masks may be applied at some or all of the hidden layers, including convolutional layers and fully connected layers. Further, the masks may be downsampled at one or more pooling layers of the CNN, to maintain a correspondence between a size of the masks and a size of an output of the one or more pooling layers. By limiting convolution operations at a plurality of convolutional layers to input from the breast area only and not from background areas, and limiting computations at one or more fully connected layers to input from the breast area only and not from background areas, a computation time may be reduced. Additionally, a performance of the CNN may be increased, as non-breast data of input images has no clinical relevance.

Figure 4A:
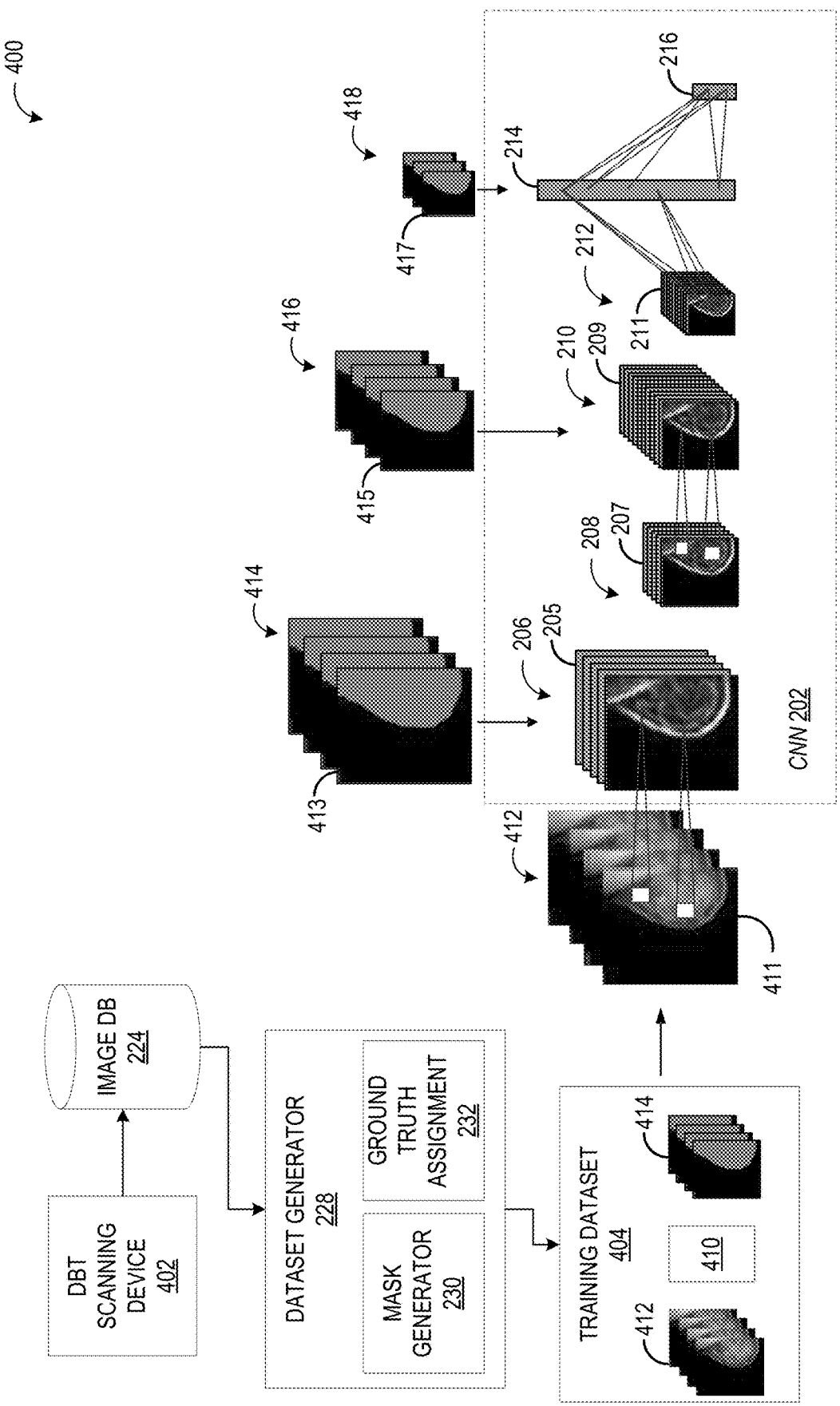
FIG. 4A shows a block diagram of an exemplary embodiment of a neural network training system for training a CNN to detect lesions in and/or classify three-dimensional (3D) DBT image volumes.
Figure 4B:
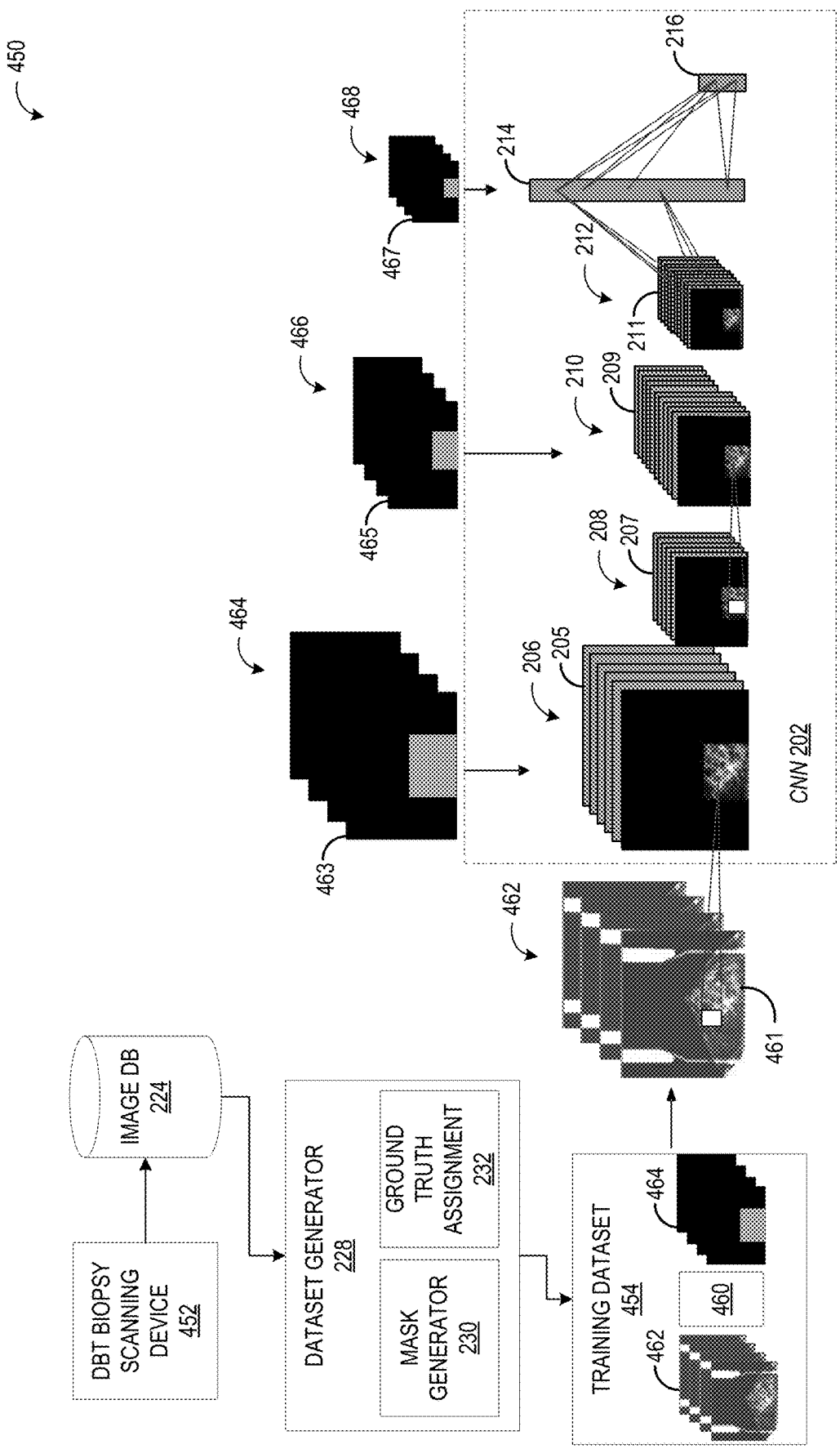
FIG. 4B shows a block diagram of an exemplary embodiment of a neural network training system for training a CNN to detect lesions in and/or classify DBT biopsy image volumes.
Figure 5:
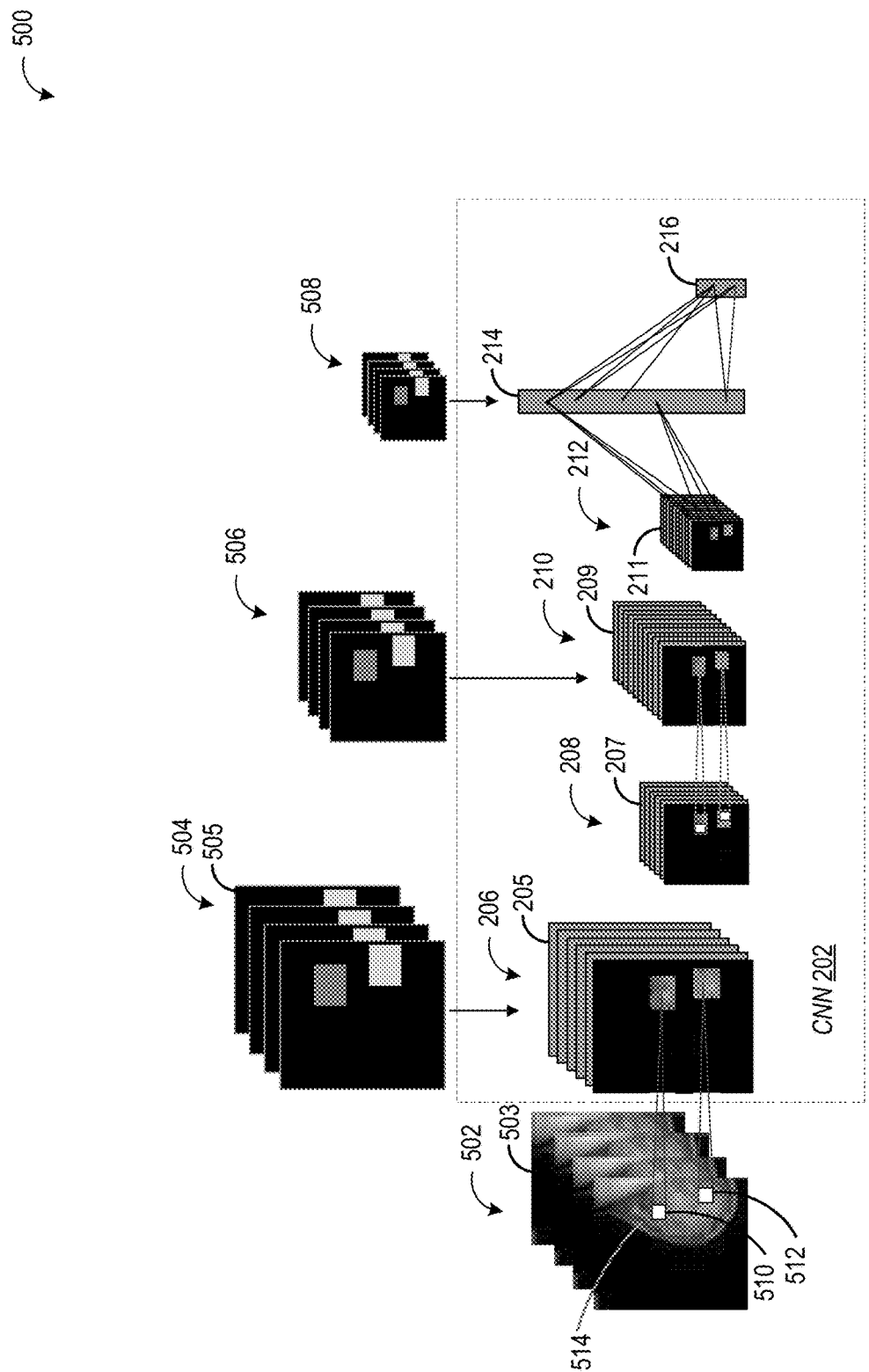
FIG. 5 shows a block diagram of an exemplary embodiment of a neural network training system for training a CNN to detect lesions in and/or classify DBT image volumes using patch-based training.

Lesions, abnormalities, and other features may be detected in mammography or tomosynthesis images by an image processing system, such as the image processing system 102 of FIG. 1. The image processing system may include a CNN, which may be trained to detect the lesions, abnormalities, and other features in a breast of a subject. For 2D FFDM images, the CNN may be trained using a neural network training system such as the neural network training system 200 of FIG. 2A. 2D breast masks may be used in each convolutional layer of the CNN, which may have an architecture such as the CNN 202 of FIG. 2A. For 2D biopsy images, the CNN may be trained using a second embodiment 250 of the neural network training system 200, as shown in FIG. 2B, where 2D biopsy window masks may be used in each convolutional layer of the CNN. For three-dimensional (3D) DBT images, the CNN may be trained using a third embodiment 400 of the neural network training system 200, as shown in FIG. 4A, where 3D breast masks are used in each convolutional layer of the CNN. For 3D DBT biopsy images, the CNN may be trained using a fourth embodiment 450 of the neural network training system 200, as shown in FIG. 4B, where 3D biopsy window masks are used in each convolutional layer of the CNN. To further decrease a training time of the CNN, the CNN may be trained using a fifth embodiment 500 of the neural network training system 200, as shown in FIG. 5, where the CNN may be trained using 2D or 3D patches. Training the CNN to learn to classify and/or detect lesions in 2D FFDM and/or biopsy images, or 3D DBT and/or DBT biopsy images, may be carried out by executing one or more operations of a method such as method 300 of FIG. 3A. The CNN may be deployed to classify and/or detect lesions in the 2D FFDM and/or biopsy images, or the 3D DBT and/or DBT biopsy images, in accordance with method 350 of FIG. 3B.

Referring to FIG. 1, an image processing system 102 of a medical imaging system 100 is shown, in accordance with an embodiment. In some embodiments, at least a portion of image processing 102 is disposed at a device (e.g., edge device, server, etc.) communicably coupled to the medical imaging system 100 via wired and/or wireless connections. In some embodiments, at least a portion of image processing system 102 is disposed at a separate device (e.g., a workstation) which can receive images from the medical imaging system 100 or from a storage device which stores the images/data generated by the medical imaging system 100.

Image processing system 102 includes a processor 104 configured to execute machine readable instructions stored in non-transitory memory 106. Processor 104 may be single core or multi-core, and the programs executed thereon may be configured for parallel or distributed processing. In some embodiments, the processor 104 may optionally include individual components that are distributed throughout two or more devices, which may be remotely located and/or configured for coordinated processing. In some embodiments, one or more aspects of the processor 104 may be virtualized and executed by remotely-accessible networked computing devices configured in a cloud computing configuration.

Non-transitory memory 106 may store a neural network module 108, a network training module 110, an inference module 112, and medical image data 114. Neural network module 108 may include a deep learning model and instructions for implementing the deep learning model to classify a breast in an input image, as described in greater detail below. Neural network module 108 may include one or more trained and/or untrained neural networks and may further include various data, or metadata pertaining to the one or more neural networks stored therein.

Non-transitory memory 106 may further store a training module 110, which comprises instructions for training one or more of the neural networks implementing a deep learning model stored in neural network module 108. Training module 110 may include instructions that, when executed by the processor 104, cause image processing system 102 to execute one or more of the steps of method 300 and/or 350 for training the one or more neural networks, described in more detail below in reference to FIGS. 3A and 3B, respectively. In some embodiments, training module 110 includes instructions for implementing one or more gradient descent algorithms, applying one or more loss functions, and/or training routines, for use in adjusting parameters of the one or more neural networks of neural network module 108. Non-transitory memory 106 may also store an inference module 112 that comprises instructions for processing and/or classifying new image data with the trained deep learning model. In some embodiments, the training module 110, the neural network module 108, and the inference module 112 may be stored and/or executed on separate devices.

Non-transitory memory 106 further stores medical image data 114. Medical image data 114 may include for example, medical images acquired via a computed tomography (CT)

scanner, an X-ray machine, an ultrasound probe, or via a different imaging modality. For example, the medical image data 114 may store mammogram images, or tomosynthesis data acquired from a breast of a patient. In some embodiments, medical image data 114 may include a plurality of training sets.

In some embodiments, the non-transitory memory 106 may include components disposed at two or more devices, which may be remotely located and/or configured for coordinated processing. In some embodiments, one or more aspects of the non-transitory memory 106 may include remotely-accessible networked storage devices configured in a cloud computing configuration.

Image processing system 102 may be operably/communicatively coupled to a user input device 132 and a display device 134. User input device 132 may comprise one or more of a touchscreen, a keyboard, a mouse, a trackpad, a motion sensing camera, or other device configured to enable a user to interact with and manipulate data within image processing system 102. Display device 134 may include one or more display devices utilizing virtually any type of technology. In some embodiments, display device 134 may comprise a computer monitor, and may display medical images. Display device 134 may be combined with processor 104, non-transitory memory 106, and/or user input device 132 in a shared enclosure, or may be peripheral display devices and may comprise a monitor, touchscreen, projector, or other display device known in the art, which may enable a user to view medical images produced by an medical imaging system, and/or interact with various data stored in non-transitory memory 106.

It should be understood that image processing system 102 shown in FIG. 1 is for illustration, not for limitation. Another appropriate image processing system may include more, fewer, or different components.

Figure 2A:
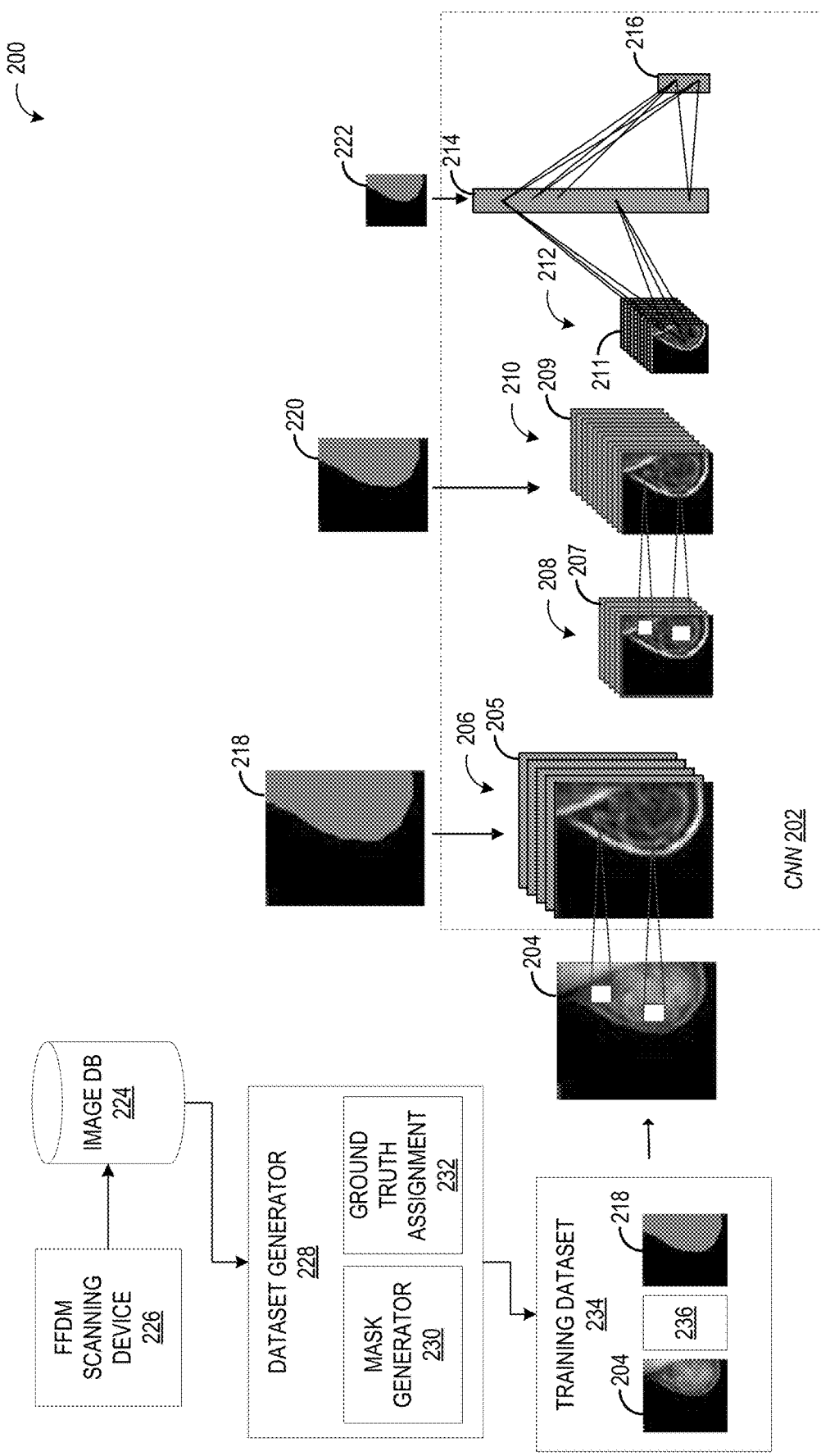
FIG. 2A shows a block diagram of an exemplary embodiment of a neural network training system for training a CNN to detect lesions in and/or classify FFDM images.
Figure 2B:
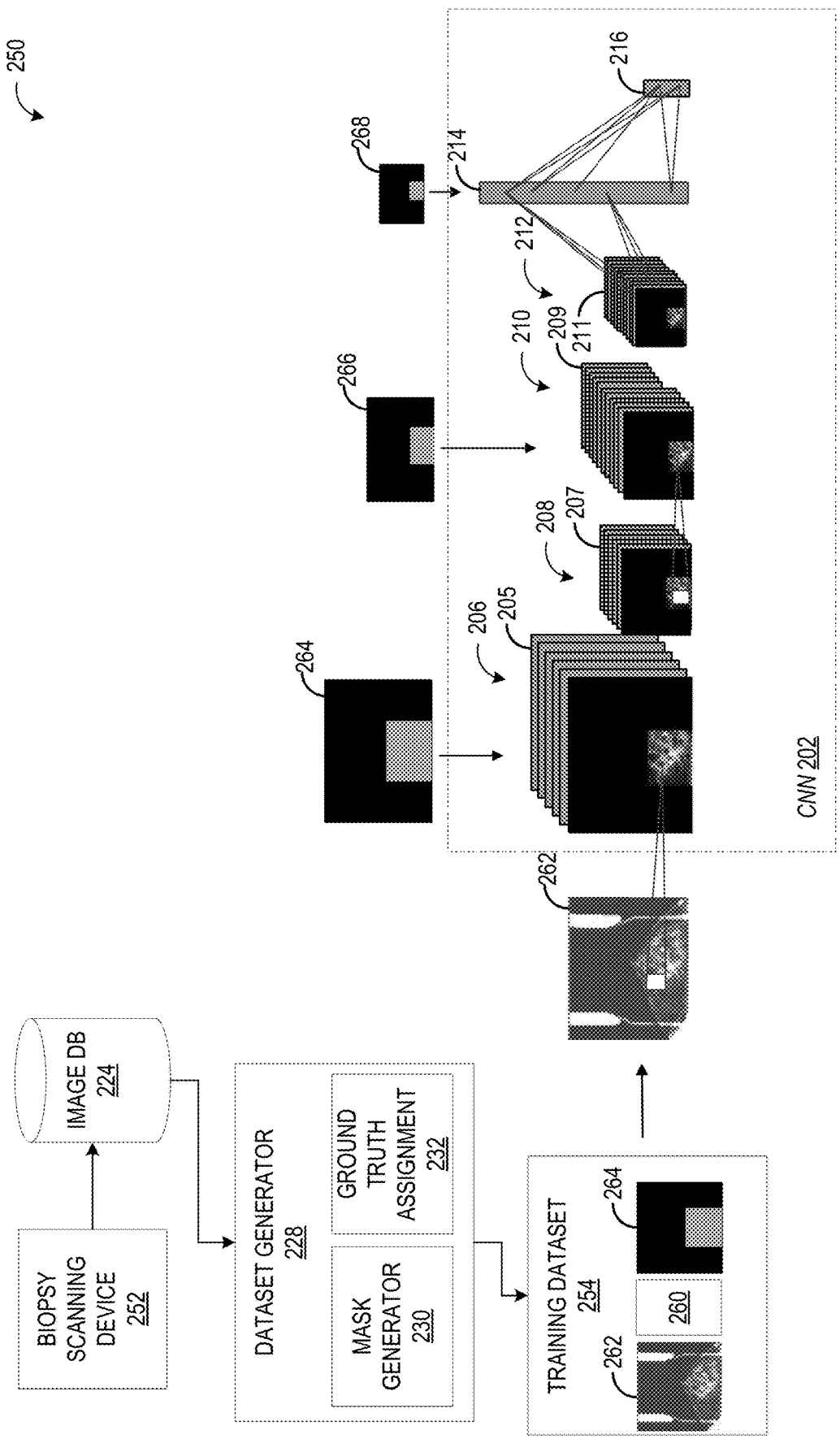
FIG. 2B shows a block diagram of an exemplary embodiment of a neural network training system for training a CNN to detect lesions in and/or classify two-dimensional (2D) biopsy images.

Referring to FIG. 2A, a neural network training system 200 is shown for a CNN 202, where the CNN 202 may be trained to detect abnormalities in FFDM images (e.g., mammograms) of a human breast. The neural network training system 200 may be implemented as part of an image processing system, such as image processing system 100 of FIG. 1 (e.g., within neural network module 108). The CNN 202 may be trained in accordance with one or more operations of a method such as method 300 of FIG. 3A. The CNN 202 may be trained on FFDM images, which may be stored in a database of the image processing system, such as the medical image data 114 of the image processing system 100 of FIG. 1. After training is completed, a trained CNN 202 may be deployed to an inference module of the image processing system, such as the inference module 112 of the image processing system 102 of FIG. 1.

The CNN 202 may be trained on a training dataset 234, where the training dataset may include a plurality of input/target training pairs. In some embodiments, the CNN 202 may be a classification network, where image/target training pairs may include an FFDM image 204 having a breast as an input into the CNN 202, and an image classification 236 of the breast as a target. For example, a first input/target training pair may include a first FFDM image 204 and a corresponding classification of 0, indicating that no abnormalities were detected in the breast. A second input/target training pair may include a second FFDM image 204 and a corresponding classification of 1, indicating that an abnormality (e.g., a lesion, tumor, etc.) was detected in the breast. In other embodiments, additional classifications may be included. For example, in one embodiment, a first classification may indicate a breast with no abnormalities, a second classification may indicate a breast with a non-malignant tumor, and a third classification may indicate a malignant tumor. In other embodiments, other histology classifications may be used, such as normal, benign, in situ, and invasive. The target image classification 236 may be considered a ground truth associated with a corresponding FFDM image 204 for the purposes of training the CNN 202.

In still other embodiments, the CNN 202 may not be a classification network, and the CNN 202 may detect a presence or a location of a lesion in an FFDM image of a breast. For example, the image/target training pairs may include an FFDM image 204 having a breast as an input into the CNN 202, and ground truth lesion information as a target. The ground truth lesion information may include an indication of whether a lesion is present or not in the FFDM image 204, and location information of the lesion. It should be appreciated that the examples provided herein are for illustrative purposes and different examples may be included without departing from the scope of this disclosure.

The neural network training system 200 may include a dataset generator 228, which may generate the input/target training pairs of the training dataset. In some embodiments, the dataset generator 228 may receive FFDM images 204 from an image database 224. The FFDM images 204 stored in the image database 224 may be generated by an FFDM scanning device 226 (e.g., an x-ray device). The classification associated with each FFDM image 204 may be assigned by a ground truth assignment process 232. Assignment of the classifications is described in greater detail below in reference to FIG. 3A.

The dataset generator 228 may also include a mask generator 230, which may generate masks for the FFDM images 204. Specifically, the FFDM image 204 of each input/target training pair of the training dataset 234 may be assigned a corresponding 2D breast mask 218. The 2D breast mask 218 may be a two dimensional (2D) array of values of a size of the corresponding FFDM image 204, with a 1:1 correspondence between each value of the 2D breast mask 218 and each pixel of the FFDM image 204. For example, a top left value in an upper left corner of the 2D breast mask 218 may be associated with a top left pixel in an upper left corner of the corresponding FFDM image 204; an adjacent value along a top row of the 2D breast mask 218 may be associated with an adjacent pixel along a top row of the corresponding FFDM image 204; and so on.

The 2D breast mask 218 may include either a first value or a second value for each pixel of the corresponding FFDM image 204. For example, the first value may be 1 and the second value may be 0. Whether a value of the 2D breast mask 218 is assigned the first value or the second value may depend on whether a corresponding pixel of the FFDM image 204 includes breast data or background data. If the corresponding pixel includes breast data (e.g., if the corresponding pixel is located within a breast portion of the FFDM image 204), the corresponding value may be assigned the first value (e.g., a 1). Alternatively, if the corresponding pixel does not include breast data (e.g., if the corresponding pixel is located outside a breast portion, such as in a background portion of the FFDM image 204), the corresponding value may be assigned the second value (e.g., a 0). Thus, the 2D breast mask 218 may establish a predefined region of the FFDM image 204 where the breast portion of the FFDM image 204 is with respect to the background portion of the FFDM image 204. The generation of the 2D breast mask 218 is described in greater detail below in reference to FIG. 3A.

The CNN 202 may include a plurality of convolutional layers, such as a first convolutional layer 206 and a second convolutional layer 210. The first convolutional layer 206 and the second convolutional layer 210 may each comprise a number of filters or kernels, which may generate an equal number of feature maps. The feature maps may aid the CNN 202 in detecting features of the FFDM image 204. For example, the first convolutional layer 206 may include five feature maps 205, corresponding to five filters, where the feature maps 205 may aid the CNN 202 in detecting lower level features of the FFDM image 204 (e.g., lines, corners, edges, etc.). The second convolutional layer 210 may include ten feature maps 209, corresponding to ten filters, where the feature maps 209 may aid the CNN 202 in detecting higher level features of the FFDM image 204. The higher level features may include abstractions of relationships between the lower level features, which may or may not be interpretable by a human. A number of feature maps 205 may be different from a number of feature maps 209, where the numbers of feature maps 205 and 209 depend on an architectural implementation of the CNN 202.

After each of the plurality of convolutional layers, the CNN 202 may include a pooling layer, such as the first pooling layer 208 and the second pooling layer 212. The CNN 202 may also include a fully connected layer 214, where each and every feature of an immediately preceding layer (e.g., the pooling layer 212) is connected with each and every input neuron of the fully connected layer 214. To avert a potentially enormous number of computations at the fully connected layer 214, the pooling layers 208 and 212 may pool outputs of immediately preceding convolutional layers 206 and 210, respectively, in order to downscale a number of features of the CNN 202.

The first pooling layer 208 and the second pooling layer 212 may each generate a set of pooled feature maps. For example, the first pooling layer 208 may include five pooled feature maps 207, corresponding to the five feature maps 205, where the pooled feature maps 207 may be downsampled versions of the feature maps 205. Similarly, the second pooling layer 212 may include ten pooled feature maps 211, corresponding to the ten feature maps 209, where the pooled feature maps 211 may be downsampled versions of the feature maps 209. A number of pooled feature maps 207 may be different from a number of pooled feature maps 211, where the numbers of pooled feature maps 207 and 211 depend on an architectural implementation of the CNN 202.

For example, each FFDM image 204 may include over 6 million pixels, based on a resolution of 2394*2850 pixels, where each of the over 6 million pixels may be inputted into the first convolutional layer 206. The first convolutional layer 206 may output a number of features almost as large as the over 6 million pixels, depending on hyper-parameters of the CNN 202 (e.g., filter size, stride). In some embodiments, to reduce a demand on memory of the neural network training system 200 entailed by multiplying such a large number of features at each layer of the CNN 202, and especially at the fully connected layer 214, the pooling layer 208 may combine outputs of the first convolutional layer 206 within a 2D sub-region to reduce an overall number of features maintained in the memory of the neural network training system 200. In some embodiments, combining the outputs may include averaging output values of the 2D sub-region to generate a single value (e.g., average pooling). In other embodiments, combining the outputs may include selecting a single value to represent the output values of the 2D sub-region, such as the highest value (e.g., max pooling). Similarly, the pooling layer 212 may combine outputs of the second convolutional layer 210, to further downscale a number of features generated by the second convolutional layer prior to performing computations of the fully connected layer 214. While two convolutional layers are depicted in FIG. 2A, it should be appreciated that other embodiments may include a greater or lesser number of convolutional layers, pooling layers, and/or fully connected layers without departing from the scope of this disclosure. The advantages of downscaling parameters of a CNN by adjusting hyper-parameters and pooling strategies are well known in the art and are outside the scope of this disclosure.

When an FFDM image 204 is inputted into the first convolutional layer 206 of the CNN 202, a corresponding 2D breast mask 218 may also be inputted into the first convolutional layer 206. The 2D breast mask 218 may selectively inhibit input into the CNN 202 from background areas of the FFDM image 204 (e.g., areas not including a human breast), as described above. In another embodiment, the 2D breast mask 218 may be inputted into the CNN 202 as an array of values comprising 1s and 0s, where each value of the array of values is multiplied by a corresponding pixel of each feature map 206 and/or by a corresponding pixel of each input 262.

Additionally, a second 2D breast mask 220 may be inputted into the second convolutional layer 210, where the second 2D breast mask 220 is a downsampled version of the 2D breast mask 218. In some embodiments, one or more downsampling operations are performed on the 2D breast mask 218 in parallel with a performing of the one or more downsampling operations on a number of features generated by the first convolutional layer 206, whereby a procedure used to downsample or downscale the features at the first pooling layer 208 is also followed to downsample the 2D breast mask 218 to generate the second 2D breast mask 220. For example, if 2D, 3*3 groups of output values of the first convolutional layer 206 are pooled at the first pooling layer 208 to generate single output values, then corresponding 2D, 3*3 groups of output values of the 2D breast mask 218 may be pooled at the first pooling layer 208 to generate single output values corresponding to the second 2D breast mask 220. In some embodiments, the 2D breast mask 218 may be downsampled within the CNN 202, while in other embodiments, the 2D breast mask 218 may be downsampled in parallel with the downsampling operations of the input image data outside the CNN 202 in accordance with a separate procedure. The separate procedure may include the same downsampling operations as the input image, or different downsampling operations. The downsampling operations of the separate procedure may depend on a pooling strategy of the CNN 202. In this way, the second 2D breast mask 220 may preserve a spatial relationship of the 2D breast mask 218 with the FFDM image 204 and a 1:1 correspondence with the feature maps 207. In the same way, a third downsampled 2D breast mask 222 may be inputted into the fully connected layer 214, along with an output of the second pooling layer 212, where the third downsampled 2D breast mask 222 is a pooled version of the second downsampled 2D breast mask 220. The fully connected layer may receive as input features of the feature maps 211 that are inside the mask, and not receive features of the feature maps 211 that are outside the mask. Alternatively, when the 2D breast mask 222 is encoded as an array of values comprising 1s and 0s, each value of the array of values may be multiplied by a corresponding pixel of each feature map 212.

The CNN 202 may generate a final output at an output layer 216, based on an output of the fully connected layer 214. In some embodiments, the output 216 may be a classification of the breast of the FFDM image 204. For example, the CNN 202 may output a classification value of 1, indicating that one or more lesions and/or abnormalities may have been detected by the CNN 202, or the CNN 202 may output a classification value of 0, indicating that no lesions and/or abnormalities were detected by the CNN 202. Other embodiments may include additional or different output values. For example, the additional or different output values may be used to distinguish between certain types of lesions or abnormalities, or to indicate a degree of seriousness of a detected lesion or tumor. In another embodiment, the CNN 202 may output a map to indicate a location of a lesion or abnormality, or something else.

As described in greater detail below in reference to FIG. 3A, a difference between the output 216 and the target classification 236 may be backpropagated through the CNN 202 in accordance with a loss function to adjust parameters of the CNN 202, whereby the CNN 202 may learn to classify new FFDM images or to detect lesions in the new FFDM images.

Referring now to FIG. 2B, a second embodiment 250 of the neural network training system 200 is shown, where the CNN 202 may be trained to detect abnormalities in a breast using a set of 2D biopsy images of the breast. During a biopsy, one or more tissue samples are extracted from the breast using a needle for subsequent analysis. The 2D biopsy images may be used to aid a clinician in guiding the needle to a precise location of a lesion which may be small. As collections of 2D biopsy images may be generated routinely as part of performing a biopsy, the collections of 2D biopsy images may represent a large amount of training data containing lesions which may be advantageously used for training the CNN 202. For example, if 2D FFDM images containing lesions are less easily obtained for training the CNN 202 than 2D biopsy images, the CNN 202 may be trained on a combination of 2D biopsy images and 2D FFDM images. Alternatively, the CNN 202 may be trained on 2D biopsy images in a first training stage, and trained on 2D FFDM images in a second training stage, or trained on 2D FFDM images in the first training stage, and trained on 2D biopsy images in the second training stage, or the CNN 202 may be trained over a plurality of training stages including 2D FFDM images and/or 2D biopsy images. After the CNN 202 has been trained, the CNN 202 may be deployed to detect and/or classify breast abnormalities in either new 2D FFDM images or new 2D biopsy images.

In some embodiments, the CNN 202 may be trained to detect lesions within a biopsy window, where the biopsy window is a scanned area of interest where a lesion may be located. In this case, the breast mask may be limited to the biopsy window in order the CNN 202 to perform convolutions only inside the biopsy window and not perform convolutions outside the biopsy window. In some embodiments, the biopsy window may be a simple geometrical shape (e.g., a quadrangle) delimited by a shape of a compression paddle used for the biopsy.

By taking into account the biopsy window in the training phase, a computation time of the CNN 202 during training may be reduced, and a performance may be improved, as irrelevant data outside the biopsy window is ignored (such as data at borders of the compression paddle). By not performing convolutions outside the biopsy window, a computation time of the CNN 202 during inference may also be reduced. During deployment of the CNN 202, while guiding the needle, the clinician may monitor a placement of a tip of the needle while watching the 2D biopsy images on a display screen. By detecting and identifying the lesion in real time as the clinician adjusts the needle, guidance cues or instructions may be provided to the clinician by the trained CNN 202 on the display screen. By training the network on both FFDM and biopsy data using the breast mask and the biopsy window mask, respectively, as additional input, a number of samples including lesions is expected to increase. Additionally, an overall detection performance may be improved when the CNN 202 is applied on new FFDM images.

Figure 3A:
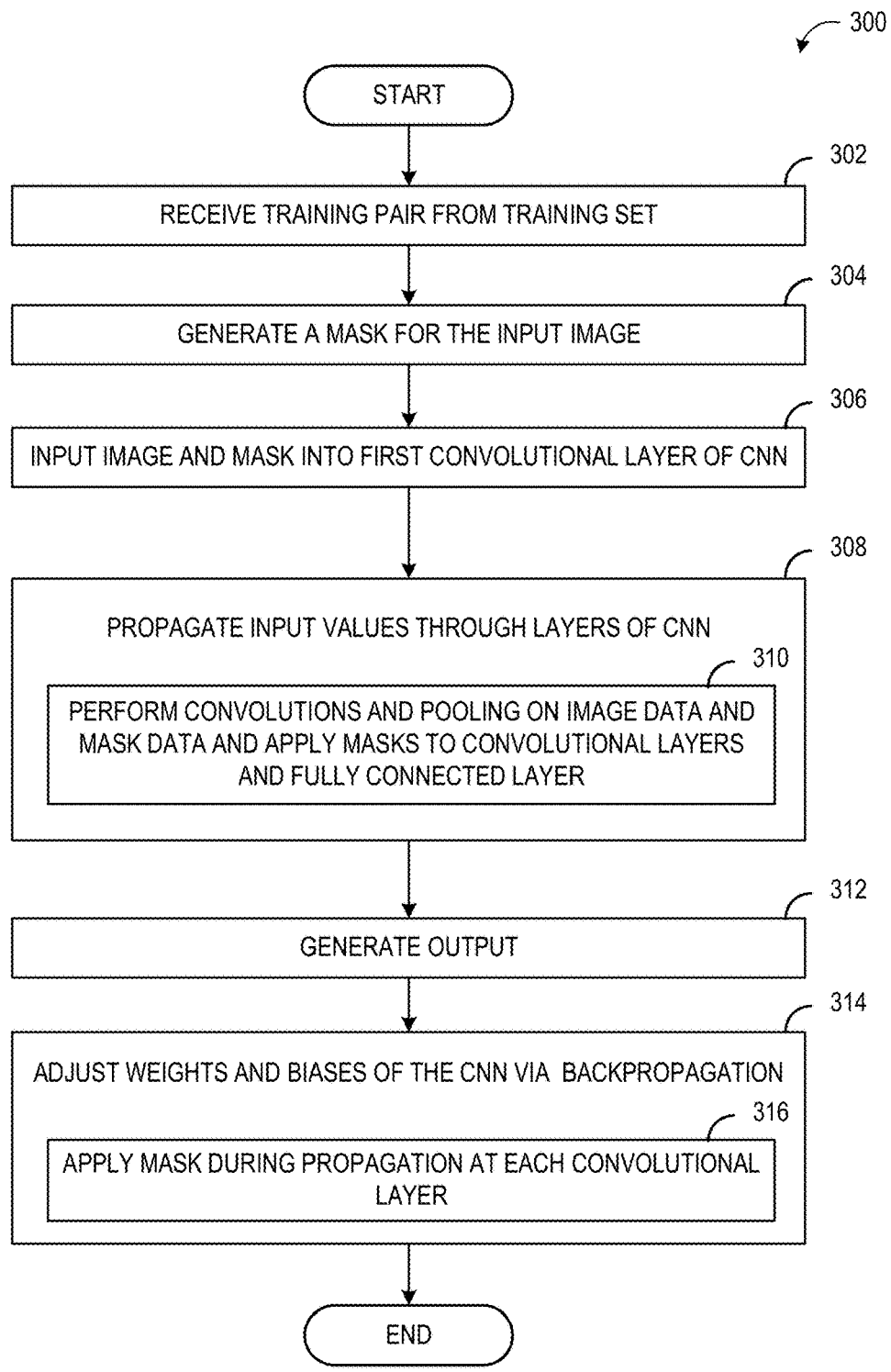
FIG. 3A shows a flowchart illustrating an exemplary method for training a CNN to detect lesions in and/or classify FFDM or 2D biopsy images.
Figure 3B:
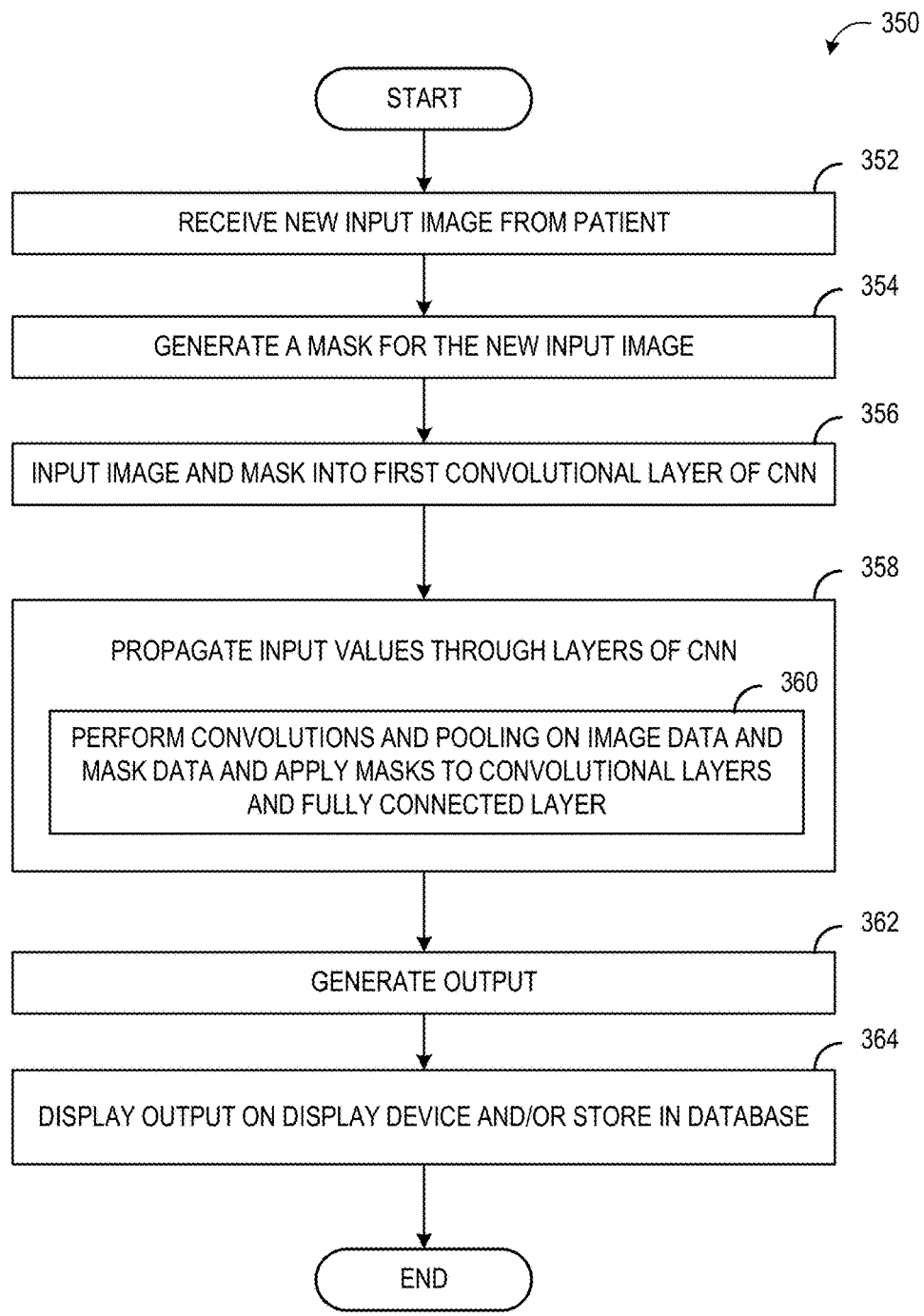
FIG. 3B shows a flowchart illustrating an exemplary method for deploying a trained CNN to detect lesions in and/or classify FFDM or 2D biopsy images.

In the second embodiment 250 of the neural network training system 200, the CNN 202 may be trained in accordance with one or more operations of a method such as method 300 of FIG. 3A, and deployed in accordance with one or more operations of a method such as method 350 of FIG. 3B. The CNN 202 may be trained on the 2D biopsy images, which may be stored in a database of the image processing system, such as the medical image data 114 of the image processing system 100 of FIG. 1. After training is completed, the trained CNN 202 may be deployed to an inference module of the image processing system, such as the inference module 112 of the image processing system 102 of FIG. 1.

In the second embodiment 250, the CNN 202 may be trained on a training dataset 254, where the training dataset may include a plurality of input/target training pairs. The plurality of image/target training pairs may include a 2D biopsy image 262 as an input into the CNN 202, and ground truth lesion information 260 as target data. The ground truth lesion information 260 may include an indication of whether a lesion is detected in the 2D biopsy image 262, and may include location information of the lesion. For example, the location information may include X,Y coordinates of the lesion, boundary information of the lesion, an extent of the lesion in one or more directions, and so forth.

The 2D biopsy images 262 stored in the image database 224 may be generated by a scanning device 226 (e.g., an x-ray machine). The ground truth associated with each 2D biopsy image 262 may be assigned by the ground truth assignment process 232 of the dataset generator 228. Assignment of the ground truths is described in greater detail below in reference to FIG. 3A.

As with the FFDM images 204 of FIG. 2A, the mask generator 230 may generate masks for the 2D biopsy images 262 in the embodiment 250. Specifically, the 2D biopsy image 262 of each input/target training pair of the training dataset 254 may be associated with a corresponding 2D biopsy window mask 264. The 2D biopsy window mask 264 may be a two dimensional array of values of a size of the corresponding 2D biopsy image 262, with a 1:1 correspondence between each value of the 2D biopsy window mask 264 and each pixel of the 2D biopsy image 262.

The 2D biopsy window mask 264 may include a first value (e.g., a 1) or a second value (e.g., a 0) for each pixel of the corresponding 2D biopsy image 262. Whether a value of the 2D biopsy window mask 264 is assigned the first value or the second value may depend on whether a corresponding pixel of the 2D biopsy image 262 lies within a 2D biopsy window of the 2D biopsy image 262. If the corresponding pixel lies within a 2D biopsy window of the 2D biopsy image 262, the corresponding value may be assigned the first value (e.g., a 1). Alternatively, if the corresponding pixel does not lie within the 2D biopsy window, the corresponding bit may be assigned the second value (e.g., a 0). Thus, the 2D biopsy window mask 264 may establish a pre-defined region within the 2D biopsy image 262 where the 2D biopsy window is located. The generation of the 2D biopsy window mask 264 is described in greater detail below in reference to FIG. 3A.

As described above in reference to FIG. 2A, the pooling layers 208 and 212 may combine outputs of the first convolutional layer 206 and the second convolutional layer 210, respectively, in accordance with an average pooling, max pooling, or different pooling technique.

When a 2D biopsy image 262 is inputted into the first convolutional layer 206 of the CNN 202, a corresponding 2D biopsy window mask 264 may also be inputted into the first convolutional layer 206. The 2D biopsy window mask 264 may selectively inhibit input into the CNN 202 from areas of the 2D biopsy image 262 that are outside the 2D biopsy window, as described above in reference to FIG. 2A. Each 2D biopsy window mask 264 may be inputted into the CNN 202 as an array of values comprising 1s and 0s, where, in some embodiments, each value of the array of values is multiplied by a corresponding pixel input of the 2D biopsy image 262 and/or a corresponding pixel output of the first convolutional layer 206. In other embodiments, a different algorithm may be used to selectively inhibit some portions of the CNN 202 based on the 2D biopsy window mask 264. For example, the 2D breast mask 264 may be inputted into the CNN 202 as an array of values comprising 1s and 0s, where each value of the array of values is multiplied by a corresponding pixel of each feature map 205.

Additionally, as described above in reference to the second 2D breast mask 220 and the third 2D breast mask 222 of FIG. 2A, in the embodiment 250, a second 2D biopsy window mask 266 may be inputted into the second convolutional layer 210. The 2D biopsy window mask 266 may be a downsampled version of the 2D biopsy window mask 264. Likewise, a third 2D biopsy window mask 268 may be inputted into the fully connected layer 214 along with an output of the second pooling layer 212, where the third 2D biopsy window mask 268 may be a downsampled version of the 2D biopsy window mask 266. The fully connected layer may receive as input features of the feature map 211 that are inside the mask, and not receive as input features of the feature map 211 that are outside the mask. Alternatively, when the 2D breast mask 268 is encoded as an array of values comprising 1s and 0s, each value of the array of values may be multiplied by a corresponding pixel of each feature map 211.

As in FIG. 2A, the CNN 202 may generate the output 216 based on the output of the fully connected layer 214. The output 216 may include lesion detection information of the breast of the 2D biopsy image 262, including an indication of whether a lesion is present in the 2D biopsy image 262 and location information of the lesion. As described in greater detail below in reference to FIG. 3A, a difference or error between the output 216 and the ground truth lesion information 260 may be backpropagated through the CNN 202 to adjust parameters of the CNN 202, whereby the CNN 202 may learn to detect and locate lesions in new 2D biopsy images.

Referring now to FIG. 3A, a flowchart of an exemplary method 300 is shown for training a CNN, such as the CNN 202 of FIGS. 2A and 2B, to detect, locate, and/or classify lesions or other abnormalities in high resolution 2D FFDM images and/or 2D biopsy images. Method 300 may be implemented as part of the neural network training system 200 of FIGS. 2A and 2B. In an embodiment, one or more operations of method 300 may be stored in non-transitory memory and executed by a processor, such as the non-transitory memory 106 and processor 104 of image processing system 102 of FIG. 1.

The CNN may be trained using a training dataset (e.g., the training dataset 234 of FIG. 2A and/or the training dataset 254 of FIG. 2B) comprising sets of input/target training pairs. Each training pair of the input/target training pairs may include an input image and target (e.g., ground truth) data of the input image. In some embodiments, the target data may be a classification of a breast of the input image. The classification may be a binary classification, where a classification of 0 may indicate, for example, that no abnormalities have been detected in the breast of the input image, and a classification of 1 may indicate, for example, that an abnormality (e.g., a tumor, a lesion, etc.) has been detected in the breast of the input image. In other embodiments, the classification may not be a binary classification, where the target classification may be one classification of a plurality of classifications. In some embodiments, the target classification may comprise a first binary encoding (e.g., a number of 1s and 0s) indicating a breast without abnormalities, a second binary encoding indicating a breast with a non-malignant tumor, a third binary encoding indicating a breast with a malignant tumor, and so on. Additional information such as a degree of invasiveness of a tumor may also be included in a binary encoding. In still other embodiments, the target data may include additional encodings for a location of an abnormality within the input image (e.g., to use for providing guidance cues to a biopsy clinician).

In some embodiments, the CNN may be an FFDM image classification network, where the input image may be a 2D FFDM image (e.g., the FFDM image 204 of FIG. 2A). In other embodiments, the CNN may be a 2D biopsy image detection and/or localization network, where the input image may be a 2D biopsy image (e.g., the 2D biopsy image 252). Additionally, method 300 may be applied a plurality of times on a same CNN to train different types of images. For example, the CNN may be trained in a first training stage to classify 2D FFDM images (e.g., mammograms), and the CNN may be trained in a second training stage to classify and/or locate 2D biopsy images, or the CNN may be trained in the first training stage to classify and/or locate 2D biopsy images, and in the second training stage to classify 2D FFDM images.

Method 300 begins at operation 302, where method 300 includes receiving a training pair comprising an input image and a target ground truth classification from a training set. In an embodiment, the training set may be stored in a training module of an image processing system, such as the training module 110 of image processing system 102 of FIG. 1.

At 304, method 300 includes generating a mask for the input image. For embodiments where the input image is an FFDM image, the mask may be a 2D breast mask, such as the 2D breast mask 218 of FIG. 2A described above. For embodiments where the input image is a 2D biopsy image, the mask may be a 2D biopsy window mask, such as the 2D biopsy window mask 218 of FIG. 2B described above. In various embodiments, the mask may be generated by a mask generator, such as the mask generator 230 of FIGS. 2A and 2B.

Any mask generating procedure known in the art may be used to generate the mask. For 2D breast masks, in some embodiments, the mask generator may use a physical or a statistical model, such as a previously trained neural network and/or a machine learning algorithm, to detect and/or segment a breast of the input image (e.g., a breast segmentation model). In other embodiments, a boundary of the breast in the input image may be detected in another way. The mask generator may subsequently generate an array of values of a size of the input image, where either a first value (e.g., a 1) or a second value (e.g., a 0) is assigned to each pixel of the input image. If a pixel of the input image is included within (or on) the boundary of the breast, the first value may be assigned to the array of values at a location corresponding to the pixel. Alternatively, if the pixel is not included within (or on) the boundary of the breast, the second value may be assigned to the array of values at the location corresponding to the pixel.

In some embodiments, for example, when dealing with tomosynthesis acquisitions, a plurality of breast masks may be generated prior to training the CNN, where each input projection image may be associated with a breast mask of the plurality of breast masks. For example, a plurality of input images of the training set may be inputted into the previously trained neural network to generate a corresponding plurality of breast masks in a first mask generation stage, and each input image of the plurality of input images may be associated with a corresponding breast mask of the corresponding plurality of breast masks in a second mask assignment stage.

When dealing with 2D breast biopsy images such as the 2D biopsy image 262 of FIG. 2B, the mask may be a 2D biopsy window mask (e.g., the 2D biopsy window mask 264 of FIG. 2B) rather than a breast mask. Image data processed by the CNN may be limited to a biopsy window using the 2D biopsy window mask, as shown in FIG. 2B. The biopsy window may be of a fixed size, and may be positioned at a fixed location of the 2D biopsy image, where the 2D biopsy window mask may be a mask array of the fixed size and fixed location. The mask array may include the first value (e.g., a 1) for pixels located within a region of the biopsy window, and the second value (e.g., a 0) for pixels located outside the region of the biopsy window. Thus, the 2D biopsy window mask may effectively crop the input image to a size and location of the biopsy window. By applying the biopsy window mask during training and deployment, a computation time of the CNN may be reduced by taking into advantage a positioning of the biopsy window, whereby areas outside the biopsy window may be ignored.

At 306, method 300 includes inputting the input image of the training pair and the mask assigned to the input image into a first convolutional layer of the CNN (e.g., the first convolutional layer 206 of the CNN 202 of FIGS. 2A and 2B). As described above, the mask may be a similarly sized mask array of values, such as 1s and 0s. In some embodiments, inputting the input image and the mask into the first convolutional layer of the CNN may include multiplying the pixel intensity value of each pixel by a corresponding value of the mask array (e.g., corresponding to a location of the pixel in the input image). As a result of multiplying the pixel intensity value of each pixel by a corresponding value of the mask array, a new adjusted array of input values may be generated, where pixel intensity values within the boundary of the breast of the input image are preserved, and pixel intensity values outside the boundary of the breast are converted to 0s. When input nodes of the CNN are activated by multiplying the new adjusted array of input values by weights of associated convolutional kernels, a portion of the input nodes where the input values are 0 (e.g., outside the boundary of the breast) may not be activated. In this way, breast pixel data or biopsy window pixel data of the input image may be used in convolutions and activations of the CNN, and pixel data not associated with the breast or within the biopsy window may not be used in convolutions and activations of the CNN.

For example, a first random pixel of the input image may lie within the boundary of the breast of the input image, and a second random pixel of the input image may lie outside the boundary of the breast of the input image (e.g., in a background of the input image). The first random pixel may have a pixel intensity value of 0.8, indicating that the first random pixel is in a relatively bright area of the image, and the second random pixel may have a pixel intensity value of 0.3, indicating that the second random pixel is in a relatively dark area of the image. When the array of pixel intensity values of the input image is inputted into the CNN along with the mask array of 1s and 0s, the pixel intensity value of 0.8 of the first random pixel may be multiplied by a corresponding 1 of the mask array, as a result of being inside the boundary of the breast, to generate a pixel intensity value of 0.8 in the new adjusted array of input values. Alternatively, the pixel intensity value of 0.3 of the second random pixel may be multiplied by a corresponding 0 of the mask array, as a result of being outside the boundary of the breast, to generate a pixel intensity value of 0 in the new adjusted array of input values. Thus, the new adjusted array of input values may include the original pixel intensity values of the area of the input image corresponding to the breast (e.g. pixels of interest), and may include input values of 0 for areas of the input image that do not correspond to the breast. During convolutions and calculation of dot products at the first convolutional layer, when the input values of 0 are multiplied by kernel weights of the first convolutional layer, resulting values will also be 0. Non-relevant pixels outside the breast are intentionally not considered in the convolution process, which may lead to a better quality outcome at the border of the breast.

At 308, method 300 includes propagating input values of the input image through layers of the network, from the input layer, through one or more hidden layers, until reaching an output layer of the CNN. As the CNN is composed of successive layers of convolutions on downsampled features, breast area information or biopsy window information (e.g., the masks) may therefore be propagated and downsampled across the network layers in order to limit the convolutions to the breast area or the biopsy window, respectively, each time a convolution occurs.

At 310, propagating input values of the input image through layers of the network may include performing convolutions and/or pooling operations on image data and mask data, and applying the masks to the convolutional layers and fully connected layer of the CNN. The image data may be derived from the input values resulting from multiplying the array of original pixel intensity values of the input image and the mask array 264, in accordance with an architecture of the CNN. For example, in reference to the CNN 202 of FIGS. 2A and 2B, convolutions may be performed on the input values at the first convolutional layer 206 of the CNN 202, resulting in the feature maps 205. The feature maps 205 outputted by the first convolutional layer 206 may be pooled at the first pooling layer 208, resulting in the pooled feature maps 207. Downsampled image data of the pooled feature maps 205 outputted by the first pooling layer 208 and multiplied with mask 266 may be inputted into the second convolutional layer 210, where convolutions may be performed on the downsampled image, resulting in the feature maps 209. The feature maps 209 outputted by the second convolutional layer 210 may be pooled at the second pooling layer 212, resulting in the pooled feature maps 211. Downsampled image data of the pooled feature maps 211 outputted by the second pooling layer 211 and multiplied with mask 268 may be inputted into the fully connected layer 214, which may generate an output of the CNN at the output layer 216.

In some embodiments, outputs of the first convolutional layer 206, the second convolutional layer 210, and the fully connected layer 214 may be modified by an activation function prior to being inputted into the first pooling layer 208, the second pooling layer 212, and the output layer 216, respectively. In various embodiments, the activation function may be a rectified linear activation function (ReLU).

Propagating input values of the input image from the input layer to the output layer of the CNN may include performing/downsampling on mask data (e.g., values such as is and 0s) of the mask array, and applying masks to the convolutional layers and the fully connected layer. In some embodiments, the downsampling performed on the mask data may be identical to the pooling performed on the input values of the input image and the resulting feature maps.

In this way, as each input image of the training set may be processed and downsampled by the CNN, a corresponding mask may be identically processed and downsampled by the CNN. At each convolutional layer, an appropriately scaled (e.g., matching a scale of the input image) mask is used to filter out data unrelated to the breast of the input image, as described above in reference to FIG. 2A. Additionally, when performing convolutions, a bias value may be added, where the bias value may be included when performing multiplications on data related to the breast of the input image, and not including the bias value when performing multiplications on data unrelated to the breast of the input image.

In some embodiments, convolutions and pooling operations may not be performed on the mask by the CNN, and the mask may be downsampled outside the CNN, with the downsampled masks being inputted back into respective convolutional and/or fully connected layers of the CNN. The mask may be downsampled via the same or similar operations as the pooling operations carried out on the input image data, or the mask may be downsampled via different operations from pooling operations carried out on the input image data. For example, a max pooling strategy may be used at a pooling layer of the CNN, while the mask may be downsampled outside the CNN to match a size of an output of the pooling layer via a different downsampling strategy.

At 312, method 300 includes generating an output of the CNN. The output may be an activation of an output layer of the CNN (e.g., the output layer 216 of FIGS. 2A and 2B). In some embodiments, the output may be a classification of the breast of the input image, as described above in reference to FIGS. 2A and 2B. The output may be based on one or more physical parameters associated with a breast examination. In some embodiments, the one or more physical parameters may include criteria of the Breast Imaging-Reporting and Data System (BI-RAD), or a similar system for rating mammographic images or image volumes based on malignancy. For example, the breast classification may be a binary encoding of a BI-RADS assessment category (e.g., BI-RADS 0 through BI-RADS 6), indicating a probability of malignancy. In other embodiments (e.g., when used for biopsy images or image volumes), the output of the CNN may include different information. For example, the one or more physical parameters may include localization information of a tumor or lesion of the breast, whereby the localization information may be used to provide guidance cues to a clinician during a biopsy.

At 314, method 300 includes adjusting a plurality of weights and biases of the CNN via backpropagation. In various embodiments, adjusting the plurality of weights and biases of the CNN may include calculating a difference between the output of the CNN and the target ground truth of the input image (e.g., the target classification 236 of FIG. 2A or the ground truth lesion information 260 of FIG. 2B) received at operation 302 and inputted into the CNN along with the input image. The plurality of weights and biases of the CNN may be adjusted based on the difference between the output and the target ground truth from a relevant training pair. The difference (or loss), as determined by a loss function, may be backpropagated through the CNN to update weights (and biases) of the convolutional layers. In some embodiments, back propagation of the loss may occur according to a gradient descent algorithm, wherein a gradient of the loss function (a first derivative, or approximation of the first derivative) is determined for each weight and bias of the CNN. Each weight (and bias) of the CNN may be updated by adding the negative of the product of the gradient determined (or approximated) for the weight (or bias) with a predetermined step size. The backpropagation may comprise computing the gradient one layer at a time, iterating backward from the last layer to the first layer. It will be noted that method 300 may be repeated until the weights and biases of the CNN converge, or the rate of change of the weights and/or biases of the CNN for each iteration of method 300 are below a threshold rate of change.

While not described in method 300, it should be appreciated that in order to avoid overfitting, training of the CNN may be periodically interrupted to validate a performance of the CNN on a test set comprising test training pairs. In one example, both the training pairs of the training set and the test training pairs of the test set may be selected at random from a larger training dataset. In some embodiments, training of the CNN may end when the performance of the CNN on the test training pairs converges (e.g., when an error rate on the test set converges on a minimum value).

At 316, adjusting the plurality of weights and biases of the CNN via backpropagation may include applying an appropriately downsampled mask during backpropagation at each convolutional layer and at one or more fully connected layers. For example, during backpropagation on 2D biopsy images under embodiment 250 of the neural network training system 200 of FIG. 2A, the third 2D biopsy window mask 268 may be applied at a fully connected layer 214; the second 2D biopsy window mask 266 may be applied at the second convolutional layer 210, and the original 2D biopsy window mask 264 may be applied at the first convolutional layer 206.

As a loss is backpropagated through the network, each node of the fully connected layer 214 of the CNN may be connected to a node of a pooled feature map 211 of the second pooling layer 212. The node of the pooled feature map 211 may receive inputs from a 3*3 pixel grouping of the second convolutional layer 210. During backpropagation, 9 weights associated with 9 nodes of a filter of the second convolutional layer 210 may be adjusted in accordance with the backpropagation algorithm. Prior to adjusting the 9 weights of the 9 nodes, the loss is backpropagated inside the pre-defined region and not outside the pre-defined region indicated by the second 2D biopsy window mask 266 used at the second convolutional layer 210 in the forward pass, where the corresponding value is a value at a location in the second 2D biopsy window mask 266 that corresponds with a location of the relevant node of the second convolutional layer 210.

Similarly, each node of the second convolutional layer 210 of the CNN may be connected to a node of a pooled feature map 207 of the first pooling layer 206. The node of the pooled feature map 207 may receive inputs from a 3*3 pixel grouping of the first convolutional layer 206. During backpropagation, 9 weights associated with 9 nodes of a filter of the first convolutional layer 206 may be adjusted in accordance with the backpropagation algorithm. Prior to adjusting the 9 weights of the 9 nodes the loss is backpropagated inside the pre-defined region and not outside the pre-defined region indicated by the original 2D biopsy window mask 264 used at the first convolutional layer 206 in the forward pass, where the corresponding value is a value at a location within the array of values of the first downsampled mask that corresponds with a location of the input image inputted into the first convolutional layer 206.

In some embodiments, the masks may not be applied at every convolutional layer or used during backpropagation (e.g., for learning). For example, the original 2D breast mask or 2D biopsy window mask may be applied only at the input layer, or the original and downsampled 2D breast masks or 2D biopsy window masks may be applied during propagation through convolutional and/or fully connected layers in a forward pass, but may not be applied during back-propagation. When the breast information is not used at some convolutional layers or for backpropagation during training, and a trained CNN is subsequently used to perform a breast classification, lesion detection, and/or lesion localization during a subsequent inference stage, a performance of the CNN may be negatively impacted.

In one embodiment, to leverage existing machine learning libraries, once trained, a 2D full background image with only 0s may be inputted into the CNN, and a set of background features outputted at a last convolutional layer 212 may be collected. When the trained CNN is subsequently deployed on a new 2D input image of the breast of the patient, applying the 2D breast masks or the 2D biopsy window masks to reduce computation time, a portion of a set of output features obtained at the last convolutional layer corresponding to an area outside a breast area (e.g., outside a mask) may be replaced with a corresponding portion of the set of background features corresponding to the area outside a breast area. By replacing the portion of the set of output features with the corresponding portion of the set of background features, a discrepancy between an output of a CNN trained with and without the mask may be reduced. Thus, available machine learning libraries that may not permit using masks may be used for training purposes, while the mask may be used for increased speed during an inference stage with a limited impact on performance and/or accuracy. In some scenarios, additional processing may be used to address issues of breast borders, wherein convolutions may involve some breast data and some background data.

Referring now to FIG. 3B, a flowchart of an exemplary method 350 is shown for deploying a CNN, such as the CNN 202 of FIGS. 2A and 2B, to detect, locate, and/or classify high resolution 2D FFDM images and/or 2D biopsy images. Method 350 may be implemented within an inference module of an image processing system, such as the inference module 112 of image processing system 102 of FIG. 1. In an embodiment, one or more operations of method 350 may be stored in non-transitory memory and executed by a processor, such as the non-transitory memory 106 and processor 104 of image processing system 102 of FIG. 1.

In some embodiments, the CNN may be an FFDM image classification network, where the input image may be a 2D FFDM image (e.g., the FFDM image 204 of FIG. 2A). In other embodiments, the CNN may be a 2D biopsy image lesion detection and/or localization network, where the input image may be a 2D biopsy image (e.g., the 2D biopsy image 252).

Method 350 begins at operation 352, where method 350 includes receiving a new input image from a patient. In various embodiments, the new input image may be scanned in by an x-ray machine for diagnosis or analysis at a clinic. In various embodiments, the new input image is one image of a plurality of new input images scanned in real time by the x-ray machine.

At 354, method 350 includes generating a mask for the new input image. For embodiments where the new input image is an FFDM image, the mask may be a 2D breast mask, such as the 2D breast mask 218 of FIG. 2A described above. For embodiments where the new input image is a 2D biopsy image, the mask may be a 2D biopsy window mask, such as the 2D biopsy window mask 218 of FIG. 2B described above. In various embodiments, the mask may be generated by a mask generator, such as the mask generator 235 of FIGS. 2A and 2B. A similar procedure may be used to generate the mask as used during training of the CNN, as described above in reference to FIG. 3A, or a different procedure may be used. For example, the mask generator may use a previously trained neural network and/or a machine learning algorithm to detect and/or segment a breast of the new input image (e.g., a breast segmentation model), or the mask generator may generate a 2D biopsy window mask in accordance with a local biopsy procedure or equipment. The mask generator may subsequently generate an array of 1s and 0s of a size of the new input image, where either a 1 or a 0 is assigned to each pixel of the new input image. If a pixel of the new input image is included within the boundary of the breast or biopsy window, a 1 may be assigned to the array of 1s and 0s at a location corresponding to the pixel. Alternatively, if the pixel is not included within the boundary of the breast or biopsy window, a 0 may be assigned to the array of 1s and 0s at the location corresponding to the pixel. If the pixel is included on the boundary of the breast or biopsy window, the mask may be dilated, or eroded, or adjusted in a different manner depending on a specific implementation.

At 356, method 350 includes inputting the new input image of the training pair and the mask assigned to the new input image into a first convolutional layer of the CNN (e.g., the first convolutional layer 206 of the CNN 202 of FIGS. 2A and 2B). As described above in reference to FIG. 3A, the new input image may be converted into an array of pixel intensity values of each pixel of the new input image, and the mask may be an similarly sized mask array of 1s and 0s. Inputting the new input image and the mask into the first convolutional layer of the CNN may include multiplying the pixel intensity value of each pixel by a corresponding value of the mask array (e.g., corresponding to a location of the pixel in the new input image). As a result of multiplying the pixel intensity value of each pixel by a corresponding value of the mask array, a new adjusted array of input values may be generated, where pixel intensity values within the boundary of the breast of the new input image are preserved, and pixel intensity values outside the boundary of the breast are converted to 0s. In some embodiments, a different algorithm may be used to selectively inhibit activation of nodes when the nodes receive input data associated with mask values indicating a background area of the new input image (e.g., where the input data does not include breast information). In this way, breast pixel data or biopsy window pixel data of the new input image may be used in convolutions and activations of the CNN, and pixel data not associated with the breast or within the biopsy window may not be used in convolutions and activations of the CNN.

At 358, method 350 includes propagating input values of the new input image through layers of the network, from the input layer, through one or more hidden layers, until reaching an output layer of the CNN. As the CNN is composed of successive layers of convolutions on downsampled features, breast area information or biopsy window information may therefore be propagated and downsampled across the network layers in order to limit the convolutions to the breast area or the biopsy window, respectively, each time a convolution occurs.

At 360, propagating input values of the new input image through layers of the network may include performing pooling operations on image data and mask data, and applying the masks to the convolutional layers and fully connected layer of the CNN as described above in reference to FIG. 3A.

In some embodiments, outputs of layers of the CNN (e.g., the first convolutional layer 206, the second convolutional layer 210, and the fully connected layer 214 of FIGS. 2A and 2B) may be modified by an activation function prior to being inputted into pooling and output layers (e.g., the first pooling layer 208, the second pooling layer 212, and the output layer 216 of FIGS. 2A and 2B) of the CNN.

Propagating input values of the new input image from the input layer to the output layer of the CNN may include performing pooling on mask data (e.g., values such as 1s and 0s), and applying masks to the convolutional layers and the fully connected layer. The pooling performed on the mask data may be identical to the pooling performed on the input values of the new input image and the resulting downsampled image data, where during training, as each new input image is processed and downsampled by the CNN, the mask may be identically processed and downsampled by the CNN. Alternatively, different operations may be used to downsample the mask data, either as part of the processing of the CNN or outside the CNN, with the downsampled masks being inputted into the CNN at relevant convolutional layers, as described above. As a result, at each convolutional layer, an appropriately scaled (e.g., matching a scale of the new input image) mask may be used to filter out data unrelated to the breast of the new input image, as described herein.

At 362, method 350 includes generating an output of the CNN. The output may be an activation of an output layer of the CNN (e.g., the output layer 216 of FIGS. 2A and 2B). The output may be a binary classification of the breast (e.g., malignant vs. non-malignant), or the output may be a binary encoding that includes various data of the breast, such as presence or absence, size, location, invasiveness, malignancy or non-malignancy of tumors/lesions, and/or other data.

At 364, method 350 includes displaying the output of the CNN on a display device of the image processing system and/or storing the output for subsequent use and/or analysis. In various embodiments, the output may be stored in a database of the image processing system (e.g., in the medical image data 114 of the image processing system 202 of FIG. 2). As described above, in embodiments where the new input image is a 2D biopsy image, location information of the classification may be used to assist guidance of a biopsy needle during a biopsy procedure.

Thus, a total number of operations performed during deployment in an inference stage of the CNN may be significantly reduced by inhibiting image data not relating to a breast or a biopsy window, while preserving image data relevant to the breast or biopsy window. Inhibiting image data not relating to a breast or a biopsy window may reduce computation time during use in examinations or biopsies in a clinic setting, resulting in faster examination times and an improved patient experience. Inhibiting image data not relating to a breast or a biopsy window may also improve a performance of the CNN in comparison with feeding the CNN full size images, resulting in improved outcomes.

The neural network training system 200 may also be used to train the CNN 202 to classify 3D image volumes, such as DBT image volumes and/or DBT biopsy image volumes, as shown in FIGS. 4A and 4B.

Referring to FIG. 4A, a third embodiment 400 of neural network training system 200 is shown, where the CNN 202 may be trained to detect abnormalities in 3D DBT image volumes (e.g., mammograms) of a human breast. The CNN 202 may be trained in accordance with one or more operations of a method such as method 300 of FIG. 3A. The CNN 202 may be trained on 3D DBT image volumes, which may be generated by a DBT scanning device 402 (e.g., an x-ray device) and stored in the image database 224 of the neural network training system 200.

The CNN 202 may be trained on a training dataset 404, where the training dataset may include a plurality of input/target training pairs. The plurality of input/target training pairs may be generated by the dataset generator 228, as described above in reference to FIG. 3A. The input/target training pairs may include a DBT image volume 412 of a breast as an input into the CNN 202, and an image volume classification or lesion localization 410 of the breast as a target. In FIG. 4A, the DBT image volume 412 is depicted as a set of 3D slices or slab 411, where each 3D slice 411 of the DBT image volume 412 has a depth corresponding to one or more voxels.

For example, a first input/target training pair may include a first DBT image volume 412 and a corresponding image volume classification of 0, indicating that no abnormalities were detected in the breast. A second input/target training pair may include a second DBT image volume 412 and a corresponding image volume classification of 1, indicating that an abnormality (e.g., a lesion, tumor, etc.) was detected in the breast. In other embodiments, additional classifications may be included, as described above in reference to FIG. 2A. In still other embodiments, the CNN 202 may not perform a classification task, and different and/or additional information may be used as ground truth target data during training of the CNN 202.

The mask generator 230 may generate masks for the DBT image volumes 412. Specifically, the DBT image volume 412 of each input/target training pair of the training dataset 234 may be assigned a corresponding 3D breast mask 414. The 3D breast mask 414 may be a three dimensional (3D) array of bits (represented by 1s and 0s) of a size and depth of the corresponding DBT image volume 412, where the 3D breast mask 414 includes a 1 or a 0 for each voxel of the corresponding DBT image volume 412. Thus, there may be a 1:1 correspondence between each bit of the 3D breast mask 414 and each voxel of the DBT image volume 412. As described above, selection of a 1 or a 0 for each bit of the 3D breast mask 414 may depend on whether a corresponding voxel of the DBT image volume 412 includes breast data or background data. As with the 3D DBT image volumes 412, the 3D breast mask 414 may comprise a sequence of 3D breast mask slices or slabs 413. Each 3D breast mask slice 413 may be represented as a 2D array of bits, where each bit may be used to mask a corresponding voxel intensity value of a corresponding 3D slice 411 of the DBT image volume 412.

In various embodiments, the 3D breast masks 414 may be generated during image reconstruction of the DBT image volume 412. For example, during the image reconstruction, 2D projection data may be acquired and back-projected to generate the 3D DBT image volume 412. Concurrently, for each projection of the 2D projection data, a breast area of the projection may be computed (e.g., via a segmentation model), and a corresponding 2D breast mask may be generated for the projection. When the DBT image volume 412 is reconstructed by back-propagating the 2D projection data, the corresponding 2D breast masks may be back-projected to generate a corresponding 3D breast mask 414.

Embodiment 400 of the neural network training system 200 may be trained in a manner substantially similar to training the neural network training system 200 on 2D FFDM images, as described by method 300 of FIG. 3A. During training of the CNN 202 in embodiment 400, the DBT image volume 412 may be inputted into the CNN 202 one 3D slice 411 at a time. For example, a 2D array of voxel intensity values of the first 3D slice 411 of the DBT image volume 412 may be inputted into the CNN 202 in the manner described in regard to 2D breast images in reference to FIG. 2A above. A 2D array of voxel intensity values of a second 3D slice 411 of the DBT image volume 412 may subsequently be inputted into the CNN 202, followed by a third 3D slice 411, and so on, until all (or a sufficient number) of the 3D slices 411 the DBT image volume 412 have been inputted into the CNN 202.

In other words, 3D image volumes may be processed by the CNN 202 as a sequence of 2D images, where voxel intensity values are substituted for pixel intensity values. Thus, propagation of image volume data through the CNN 202 in a forward pass and backpropagation of loss data during a weight adjustment (e.g., learning) phase may be carried out as described in method 300 of FIG. 3A. In another embodiment, the CNN 202 may receive as input a 3D volume along with a 3D mask 306, allowing 3D convolutions and 3D pooling operations to correlate information from neighboring slices or slabs. When a DBT image volume 412 is inputted into the first convolutional layer 206 of the CNN 202, a corresponding 3D breast mask 414 may also be inputted into the first convolutional layer 206. The 3D breast mask 414 may selectively inhibit input into the CNN 202 from background areas of the DBT image volume 412 (e.g., areas not including a human breast), as described above. Each 3D breast mask 414 may be inputted into the CNN 202 as an array of values comprising 1s and 0s, where each value of the array of values is multiplied by a corresponding voxel input of the DBT image volume 412. In addition, inputting the input image and the mask into the first convolutional layer of the CNN may include using the mask at each voxel to determine whether convolution shall be performed or not at the considered voxel.

In the manner described above in reference to FIG. 2A, a second 3D breast mask 416 comprising a sequence of 3D image data slices 415 may be inputted into the second convolutional layer 210, where the second 3D breast mask 416 is a downsampled version of the 3D breast mask 414, and a third downsampled 3D breast mask 418 comprising a sequence of 3D image data slices 415 may be inputted into the fully connected layer 214, along with an output of the second pooling layer 212. As a result of applying the 3D breast masks 414, 416, and 418 during convolutions, a substantial percentage of a total number of computations performed during training may be avoided, or may entail multiplying by 0 when performed, thereby reducing a computation time and performance of the CNN 202 during training.

After training, the CNN may be deployed as described in method 350 of FIG. 3B, where input DBT image volumes are received as opposed to 2D FFDM or 2D biopsy images.

A 3D breast mask may be generated or selected for a patient (e.g., using the mask generator 230) in the manner described above in relation to FIG. 2A, and masked voxel intensity values may be propagated through the trained CNN 202 to produce an output classification. A computational time taken during deployment of the CNN 202 on the patient may be similarly reduced.

FIG. 4B shows a fourth embodiment 450 of the neural network training system 200 is shown, where the CNN 202 may be trained to detect abnormalities in 3D DBT biopsy image volumes of a breast. The CNN 202 may be trained to detect lesions within a biopsy window, where the biopsy window is a scanned area of interest where a lesion may be located, and where image data outside the biopsy window may be ignored. By not performing convolutions outside the biopsy window, a computation time of the CNN 202 during training and inference may be reduced, as described above. During deployment of the CNN 202, guidance cues or instructions may be provided to a clinician by the trained CNN 202 on a display screen (e.g., of an image processing system such as the image processing system 102 of FIG. 1) while guiding a needle (e.g., to extract a tissue sample).

The CNN 202 may once again be trained in accordance with one or more operations of method 300 of FIG. 3A, and deployed in accordance with one or more operations of method 350 of FIG. 3B. The CNN 202 may be trained on the 3D biopsy image volumes, which may be stored in the image DB 224. After training is completed, the trained CNN 202 may be deployed to an inference module of the image processing system, such as the inference module 112 of the image processing system 102 of FIG. 1.

In the fourth embodiment 450 of the neural network training system 200, the CNN 202 may be trained on a training dataset 454, where the training dataset may include a plurality of input/target training pairs. The plurality of input/target training pairs may be generated by the dataset generator 228, as described above in reference to FIG. 3A. The input/target training pairs may include a 3D biopsy image volume 462 of a breast as an input into the CNN 202, and image volume ground truth data 460 of the breast as target data. In FIG. 4B, the 3D biopsy image volume 462 is depicted as a set of 3D slices 461, where each 3D slice 461 of the 3D biopsy image volume 462 has a depth of 1 voxel.

The 3D biopsy image volumes 462 stored in the image database 224 may be generated by a DBT biopsy scanning device 452 (e.g., an x-ray machine). The ground truth data associated with each 3D biopsy image volume 462 may be assigned by the ground truth assignment process 232 of the dataset generator 228, as described above in reference to FIG. 3A.

As with the DBT image volumes 412 of FIG. 4A, the mask generator 230 may generate masks for the 3D biopsy image volumes 462. Specifically, the 3D biopsy image volume 462 of each input/target training pair of the training dataset 454 may be associated with a corresponding 3D biopsy window mask 464, comprising a sequence of 3D biopsy window mask slices 463, with a 1:1 correspondence between each bit of the 3D biopsy window mask 464 and each voxel of the 3D biopsy image volume 462. A selection of a 1 or a 0 for each bit of the 3D biopsy window mask 464 may depend on whether a corresponding voxel of the 3D biopsy image volume 462 lies within a 3D biopsy window of the 3D biopsy image volume 462.

Embodiment 450 of the neural network training system 200 may be trained in a manner substantially similar to training the neural network training system 200 on 3D DBT images, as described above and by method 300 of FIG. 3A.

During training of the CNN 202 in embodiment 450, the 3D biopsy image volume 462 may be inputted into the CNN 202 one 3D slice 461 at a time.

When a 3D biopsy image volume 462 is inputted into the first convolutional layer 206 of the CNN 202, a corresponding 3D biopsy window mask 464 may also be inputted into the first convolutional layer 206. The 3D biopsy window mask 464 may selectively inhibit input into the CNN 202 from areas of the 3D biopsy image volume 462 outside the biopsy window, as described above in reference to FIG. 2B. Each 3D biopsy window mask 464 may be inputted into the CNN 202 as an array of values comprising 1s and 0s, where each value of the array of values is multiplied by a corresponding voxel input of the 3D biopsy image volume 462. In addition, inputting the input image and the mask into the first convolutional layer of the CNN may include using the mask at each voxel to determine whether convolution shall be performed or not at the considered voxel.

In the manner described above in reference to FIG. 2A, a second 3D biopsy window mask 466 comprising a sequence of 3D biopsy window mask slices 465 may be inputted into the second convolutional layer 210, where the second 3D biopsy window mask 466 is a downsampled version of the 3D biopsy window mask 464. A third downsampled 3D biopsy window mask 468 comprising a sequence of 3D biopsy window mask slices 467 may be inputted into the fully connected layer 214, along with an output of the second pooling layer 212. As a result of applying the 3D biopsy window masks 464, 466, and 468 during convolutions, a substantial percentage of a total number of computations performed during training may be avoided or may entail multiplying by 0, thereby reducing a computation time of the CNN 202 during training and deployment. Further, the trained CNN 202 may be used to generate guidance cues for a clinician on a display screen of an image processing system (e.g., the image processing system 102 of FIG. 1), as described in relation to method 350 of FIG. 3B.

Turning to FIG. 5, a fifth embodiment 500 of the neural network training system 200 is shown, where patch-based training is used to train the CNN 202 on a 3D image volume 502. The 3D image volume 502 is represented in FIG. 500 as a set of 4 slices or slabs 503. In some embodiments, masks may be used to improve network performance and reduce computation time when using patch-based training, where the CNN is trained using subsets of image data from a set of patches of an input image rather than a full image. The set of patches may correspond to ROIs of a breast, including both healthy ROIs and ROIs with abnormalities. FIG. 5 shows an example 3D patch 510 and an example 3D patch 512 of a breast 514 of a 3D image volume 502.

In a typical implementation, the set of patches may have a fixed size, and the image input may be designed to fit with the patch size. A CNN may be trained on the patches and then resized to fit with full size image. However, patch size and lesion size may not be well matched. Small patches may not allow capturing a full extent of large lesions, such as spiculated masses. On the other hand, with large patches, pixels representing small clusters of calcs might be underrepresented. A typical approach is to warp a lesion area to fit the patch size. However, warping the lesion area may result in a change in image resolution that may negatively impact the network performance, especially when dealing with features of lesions close to a detector resolution.

As disclosed herein, masks may be used to avoid issues caused by warping the lesion area to fit the patch size. The CNN 202 may be sized for handling full-size images or image volumes, while the learning process may be limited to voxels (or pixels, in embodiments with 2D images) included in the patches by using a 3D patch mask 504. The 3D patch mask 504 is shown in FIG. 5 as a set of 3D slices 505, where the slices 505 may each correspond to the slices 503 of the 3D image volume 502. Each slice 505 of the patch mask 504 may comprise an array of 1s and 0s, where 0s are assigned to voxels outside of the 3D patches 510 and 512, and 1s are assigned to voxels inside the 3D patches 510 and 512. Using this approach, the patch size may be allowed to vary to optimally adapt to each lesion size. In some embodiments, a non-lesion patch mask 504 may be generated by a computer, which may not overlap with lesion patches.

As described above in relation to the 2D and 3D breast masks and biopsy window masks, propagating, downsampling, and backpropagating image data at locations of patches may increase a performance of the CNN while further reducing computation time. For example, the patch mask 504 may be downsampled to generate a first downsampled patch mask 506, which may be inputted into the second convolutional layer 210. The first downsampled patch mask 506 may be further downsampled to generate a second downsampled patch mask 508, which may be inputted into the fully connected layer 210. The patch masks 504, 506, and 508 may also be applied for weight adjustments during backpropagation, as described above in relation to the 3D breast masks.

Thus, a total number of operations and a complexity of calculations performed during training and deployment of the CNN 202 may be significantly reduced by inhibiting image data not relating to a breast or image data outside a biopsy window, while preserving image data relevant to the breast or biopsy window, using masks that are applied at all layers of the CNN 202. The masks may be downsampled along with input images during propagation, to preserve a 1:1 correspondence between the masks and the input images. The proposed approach not only facilitates a reduction in computation time, it also may improve a performance of the CNN 202, in terms of success in performing a classification or lesion detection task on the breasts, in comparison with feeding the CNN 202 full size images, as background data may not carry clinical information. Additionally, masks may also be used during a training stage with patches to reduce computation time. By reducing computation time, deep learning models may be created, updated, and refined more rapidly, leading to better patient outcomes. Further, a duration of an examination may be reduced, leading to an improved customer experience.

A technical effect of applying masks to inhibit image data not relating to a breast or image data outside a biopsy window during training of a CNN, at every convolutional layer of the CNN, is that a computation time of the CNN during training and deployment may be reduced.

The disclosure also provides support for a method for an image processing system, comprising: generating an output of a trained convolutional neural network (CNN) of the image processing system based on an input image, including a pre-defined region of the input image as an additional input into at least one of a convolutional layer and a fully connected layer of the CNN to limit computations to input image data inside the pre-defined region, and storing the output and/or displaying the output on a display device. In a first example of the method, including the pre-defined region of the input image as an additional input into the at least one of a convolutional layer and a fully connected layer of the CNN further includes: associating a mask with at least one convolutional layer of the CNN, mapping the mask to an input of the at least one convolutional layer, performing convolutions on input data inside the pre-defined region, and not performing convolutions on input image data outside the pre-defined region. In a second example of the method, optionally including the first example, including the pre-defined region of the input image as an additional input into the at least one of a convolutional layer and a fully connected layer of the CNN further includes: associating a mask with at least one fully connected layer of the CNN, mapping the mask to an input of the at least one fully connected layer, and calculating an output of the at least one fully connected layer based on input data inside the pre-defined region and not based on input data outside the pre-defined region. In a third example of the method, optionally including one or both of the first and second examples, mapping the mask to a feature input of the at least one convolutional layer further comprises downsampling and/or resizing the mask associated with a preceding layer of the CNN. In a fourth example of the method, optionally including one or more or each of the first through third examples, the mask is an array of values of a same set of dimensions as an input into the at least one convolutional layer, each value of the array of values corresponding to a respective pixel or feature of the input, and where a first value is assigned to the array if the respective pixel or feature is inside the pre-defined region, and a second value is assigned to the array if the respective pixel or feature is outside the pre-defined region. In a fifth example of the method, optionally including one or more or each of the first through fourth examples, the method further comprises: multiplying an input and/or an output of the at least one convolutional layer with a value at a corresponding spatial position of the mask. In a sixth example of the method, optionally including one or more or each of the first through fifth examples, the method further comprises: during a training stage of the CNN, at least one of: including the mask as an additional input into at least one convolutional layer of the CNN to perform convolutions on input image data inside the pre-defined region, and not perform convolutions on input image data outside the pre-defined region, and including the mask as an additional input into at least one fully connected layer of the CNN to activate nodes based on input image data inside the pre-defined region, and not activate nodes based on input image data outside the pre-defined region. In a seventh example of the method, optionally including one or more or each of the first through sixth examples, the method further comprises: during the training stage, backpropagating a result of a loss function through nodes of the CNN, using the mask at the at least one convolutional layer of the CNN to adjust weights of the CNN based on loss backpropagation inside the pre-defined region and not outside the pre-defined region. In an eighth example of the method, optionally including one or more or each of the first through seventh examples, the method further comprises: during a training stage of the CNN, applying the mask at only an input layer of the CNN to assign the second value to pixels of the input image outside the pre-defined region, during an inference stage of the CNN: inputting a background input image into the CNN, all pixel intensity values of the background input image equal to the second value, obtaining a set of background features as an output of a last convolutional layer of the CNN, inputting a new input image into the CNN, replacing features obtained as an output of the last convolutional layer outside the pre-defined region with corresponding features of the set of background features, and generating an output of the CNN using the replaced weights. In a ninth example of the method, optionally including one or more or each of the first through eighth examples, the pre-defined region is composed of one or more areas of a breast, including normal and abnormal areas of the breast. In a tenth example of the method, optionally including one or more or each of the first through ninth examples, the mask is based on a pre-defined region delimited by one of a shape of a compression paddle or a shape of a biopsy window.

The disclosure also provides support for an image processing system comprising: a convolutional neural network (CNN), a training dataset of images, the training dataset including a plurality of training pairs, each training pair including an input image of a breast and a ground truth data of the breast, a processor communicably coupled to a non-transitory memory storing the CNN and including instructions that when executed cause the processor to define a region of the breast of each input image of each training pair, where image data in the region includes breast information and where image data not in the region does not include the breast information, during training of the CNN, input the breast information into each layer of the CNN during propagation and during backpropagation, and deploy the CNN to generate an output, and display the output on a display device and/or store the output in a database of the image processing system. In a first example of the system, inputting the breast information into each layer of the CNN during propagation and during backpropagation includes: during propagation, at each layer of the CNN, applying a mask to perform convolutions on input data inside the pre-defined region, and not perform convolutions on input image data outside the pre-defined region, and during backpropagation, at each layer of the CNN, applying the mask when using a gradient descent algorithm where weights are adjusted at nodes of the CNN based on loss backpropagation inside the pre-defined region and not outside the pre-defined region. In a second example of the system, optionally including the first example, applying the mask at each layer of the CNN further includes: performing a downsampling operation to the mask at each pooling layer of the CNN, and applying a downsampled mask at a layer subsequent to each pooling layer. In a third example of the system, optionally including one or both of the first and second examples, the output includes at least one of an indication of a presence of a lesion of the breast and location information of the lesion. In a fourth example of the system, optionally including one or more or each of the first through third examples, the CNN is trained using patch-based training, and the pre-defined region is a 2D or 3D patch used during the patch-based training.

The disclosure also provides support for a method for a convolutional neural network (CNN), comprising: deploying the CNN to detect an abnormality in an input image during an inference stage, and applying convolutional filters of the CNN to a first region of the input image, and not applying convolutional filters to a second region of the input image, wherein the first region and the second region are specified by a mask. In a first example of the method, the first region does not intersect with the second region, and wherein a total area of the input image is equal to a total area of the first region added to a total area of the second region. In a second example of the method, optionally including the first example, the mask is an array of binary values, wherein values of the array corresponding to the first region are designated with a 1, and wherein values of the array not corresponding to the first region are designated with a 0. In a third example of the method, optionally including one or both of the first and second examples, the mask is downsampled and propagated through layers of the CNN.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method for an image processing system, comprising:
generating an output of a trained convolutional neural network (CNN) of the image processing system based on an input image, including a pre-defined region of the input image as an additional input into at least one of a convolutional layer and a fully connected layer of the CNN to limit computations to input image data inside the pre-defined region; and
storing the output and/or displaying the output on a display device;
wherein including the pre-defined region of the input image as an additional input into the at least one of a convolutional layer and a fully connected layer of the CNN further includes:
associating a mask with at least one convolutional layer of the CNN;
mapping the mask to an input of the at least one convolutional layer;
performing convolutions on input data inside the pre-defined region, and
not performing convolutions on input image data outside the pre-defined region.

2. The method of claim 1, wherein mapping the mask to a feature input of the at least one convolutional layer further comprises downsampling and/or resizing the mask associated with a preceding layer of the CNN.

3. The method of claim 1, wherein the mask is an array of values of a same set of dimensions as an input into the at least one convolutional layer, each value of the array of values corresponding to a respective pixel or feature of the input, and where a first value is assigned to the array if the respective pixel or feature is inside the pre-defined region, and a second value is assigned to the array if the respective pixel or feature is outside the pre-defined region.

4. The method of claim 3, further comprising:
multiplying an input and/or an output of the at least one convolutional layer with a value at a corresponding spatial position of the mask.

5. The method of claim 3, further comprising:
during a training stage of the CNN, applying the mask at only an input layer of the CNN to assign the second value to pixels of the input image outside the pre-defined region;
during an inference stage of the CNN:
inputting a background input image into the CNN, all pixel intensity values of the background input image equal to the second value;
obtaining a set of background features as an output of a last convolutional layer of the CNN;
inputting a new input image into the CNN;
replacing features obtained as an output of the last convolutional layer outside the pre-defined region with corresponding features of the set of background features; and
generating an output of the CNN using the replaced weights.

6. The method of claim 1, further comprising:
during a training stage of the CNN, at least one of:
including the mask as an additional input into at least one convolutional layer of the CNN to perform convolutions on input image data inside the pre-defined region, and not perform convolutions on input image data outside the pre-defined region; and
including the mask as an additional input into at least one fully connected layer of the CNN to activate nodes based on input image data inside the pre-defined region, and not activate nodes based on input image data outside the pre-defined region.

7. The method of claim 6, further comprising, during the training stage, backpropagating a result of a loss function through nodes of the CNN, using the mask at the at least one convolutional layer of the CNN to adjust weights of the CNN based on loss backpropagation inside the pre-defined region and not outside the pre-defined region.

8. The method of claim 1, wherein the pre-defined region is composed of one or more areas of a breast, including normal and abnormal areas of the breast.

9. The method of claim 1, wherein the mask is based on a pre-defined region delimited by one of a shape of a compression paddle or a shape of a biopsy window.

10. A method for an image processing system, comprising:
generating an output of a trained convolutional neural network (CNN) of the image processing system based on an input image, including a pre-defined region of the input image as an additional input into at least one of a convolutional layer and a fully connected layer of the CNN to limit computations to input image data inside the pre-defined region; and
storing the output and/or displaying the output on a display device;
wherein including the pre-defined region of the input image as an additional input into the at least one of a convolutional layer and a fully connected layer of the CNN further includes:
associating a mask with at least one fully connected layer of the CNN;
mapping the mask to an input of the at least one fully connected layer; and calculating an output of the at least one fully connected layer based on input data inside the pre-defined region and not based on input data outside the pre-defined region.

11. An image processing system comprising:
a convolutional neural network (CNN);
a training dataset of images, the training dataset including a plurality of training pairs, each training pair including an input image of a breast and a ground truth data of the breast;
a processor communicably coupled to a non-transitory memory storing the CNN and including instructions that when executed cause the processor to:
define a region of the breast of each input image of each training pair, where image data in the region includes breast information and where image data not in the region does not include the breast information;
during training of the CNN:
during propagation, at each layer of the CNN, apply a mask to perform convolutions on input data inside the pre-defined region and not perform convolutions on input image data outside the pre-defined region; and
during backpropagation, at each layer of the CNN, apply the mask when using a gradient descent algorithm such that weights are adjusted at nodes of the CNN based on loss backpropagation inside the pre-defined region and not outside the pre-defined region; and
deploy the CNN to generate an output, and display the output on a display device and/or store the output in a database of the image processing system.

12. The system of claim 11, wherein further includes further instructions are stored in the memory that when executed cause the processor to:
perform a downsampling operation to the mask at each pooling layer of the CNN, and
apply a downsampled mask at a layer subsequent to each pooling layer.

13. The system of claim 11, wherein the output includes at least one of an indication of a presence of a lesion of the breast and location information of the lesion.

14. The system of claim 11, wherein the CNN is trained using patch-based training, and the pre-defined region is a 2D or 3D patch used during the patch-based training.

15. A method for a convolutional neural network (CNN), comprising:
deploying the CNN to detect an abnormality in an input image during an inference stage; and
applying convolutional filters of the CNN to a first region of the input image, and not applying convolutional filters to a second region of the input image, wherein the first region and the second region are specified by a mask that is downsampled and propagated through layers of the CNN.

16. The method of claim 15, wherein the first region does not intersect with the second region, and wherein a total area of the input image is equal to a total area of the first region added to a total area of the second region.

17. The method of claim 15, wherein the mask is an array of binary values, wherein values of the array corresponding to the first region are designated with a 1, and wherein values of the array not corresponding to the first region are designated with a 0.

* * * * *